(12) United States Patent
Hamada et al.

(10) Patent No.: US 8,852,506 B2
(45) Date of Patent: Oct. 7, 2014

(54) SAMPLE ANALYZER AND METHOD OF NOTIFYING USER BY THE SAME

(75) Inventors: Yuichi Hamada, Kobe (JP); Keisuke Kuwano, Kobe (JP)

(73) Assignee: Sysmex Corporation (JP)

( * ) Notice: Subject to any disclaimer, the term of this patent is extended or adjusted under 35 U.S.C. 154(b) by 653 days.

(21) Appl. No.: 13/074,478

(22) Filed: Mar. 29, 2011

(65) Prior Publication Data

US 2011/0244580 A1 Oct. 6, 2011

(30) Foreign Application Priority Data

Mar. 30, 2010 (JP) ................. 2010-078995

(51) Int. Cl.
*G01N 35/00* (2006.01)
*G01N 35/10* (2006.01)
*G01N 35/04* (2006.01)
*G01N 1/31* (2006.01)
*G01N 15/14* (2006.01)

(52) U.S. Cl.
CPC .. *G01N 35/00712* (2013.01); *G01N 2035/0405* (2013.01); *G01N 35/1002* (2013.01); *G01N 2035/0436* (2013.01); *G01N 1/31* (2013.01); *G01N 15/14* (2013.01); *G01N 35/00663* (2013.01); *G01N 35/00732* (2013.01); *G01N 2035/00673* (2013.01); *G01N 2035/00811* (2013.01); *G01N 2035/009* (2013.01); *G01N 2035/0091* (2013.01)
USPC ............................................. 422/63; 436/43

(58) Field of Classification Search
CPC ................. G01N 35/00663; G01N 2035/0405
See application file for complete search history.

(56) References Cited

U.S. PATENT DOCUMENTS

| | | | |
|---|---|---|---|
| 2005/0123445 A1* | 6/2005 | Blecka et al. | 422/64 |
| 2008/0063570 A1* | 3/2008 | Fujino et al. | 422/99 |

FOREIGN PATENT DOCUMENTS

| | | | |
|---|---|---|---|
| JP | 05-172823 A | | 7/1993 |
| JP | 10-096733 A | | 4/1998 |
| JP | 10-282099 A | | 10/1998 |
| JP | 2003-083998 A | | 3/2003 |
| JP | 2003-201004 | * | 7/2003 |
| JP | 2007-147627 A | | 6/2007 |
| JP | 2009-174942 A | | 8/2009 |

* cited by examiner

*Primary Examiner* — P. Kathryn Wright
(74) *Attorney, Agent, or Firm* — Brinks Gilson & Lione

(57) ABSTRACT

A sample analyzer comprising: a first container set section in which a first reagent container, wherein the first container set section includes a first operating section which is operated by a user when setting the first reagent container; a first detector configured to detect an operation of the first operating section; a second container set section in which a second reagent container, wherein the second container set section includes a second operating section which is operated by the user when setting the second reagent container; a second detector configured to detect an operation of the second operating section; an output section; and a controller configured to control the output section to output a predetermined notification, if the second detector detects the operation of the second operating section by the user when it is required to set the first reagent container in the first container set section.

13 Claims, 23 Drawing Sheets

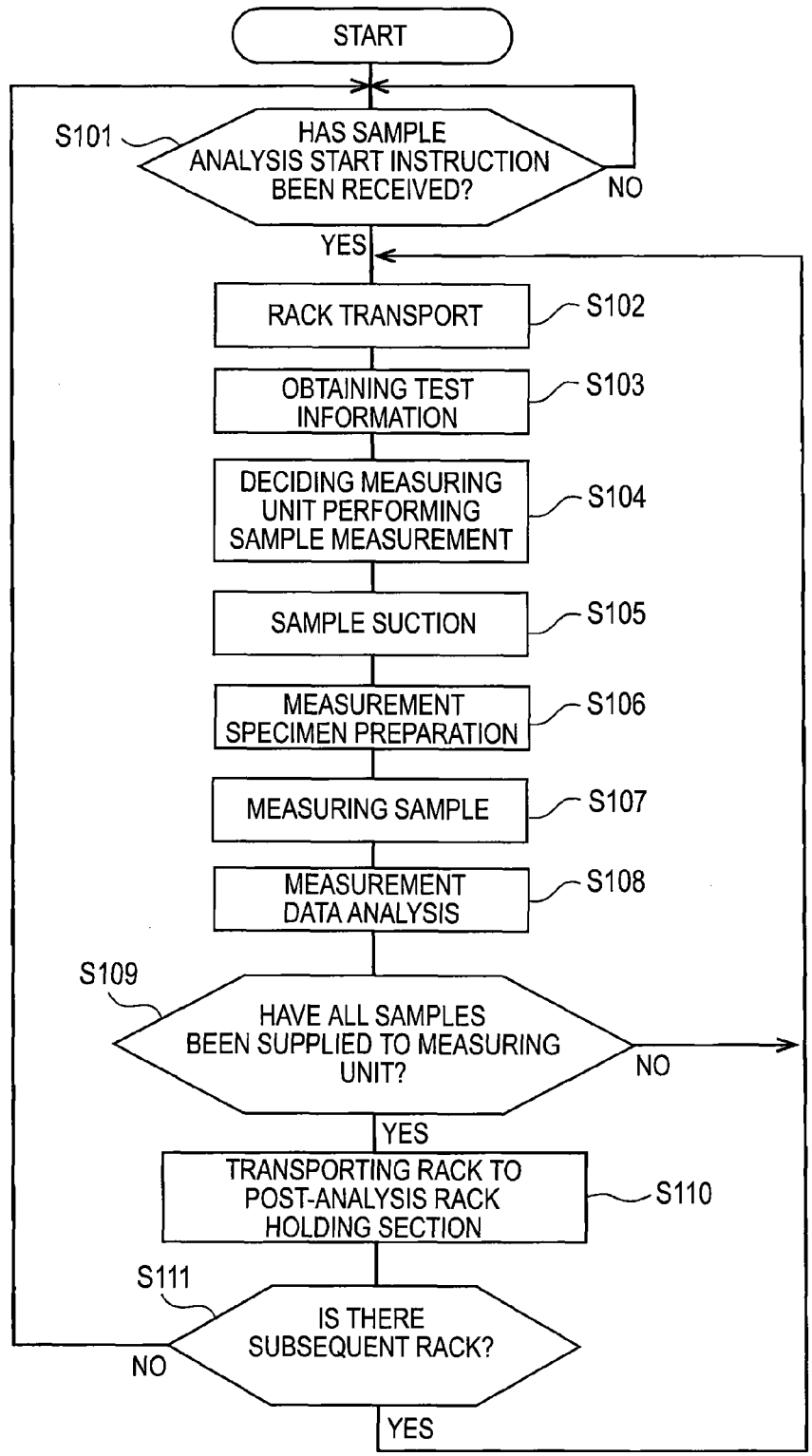

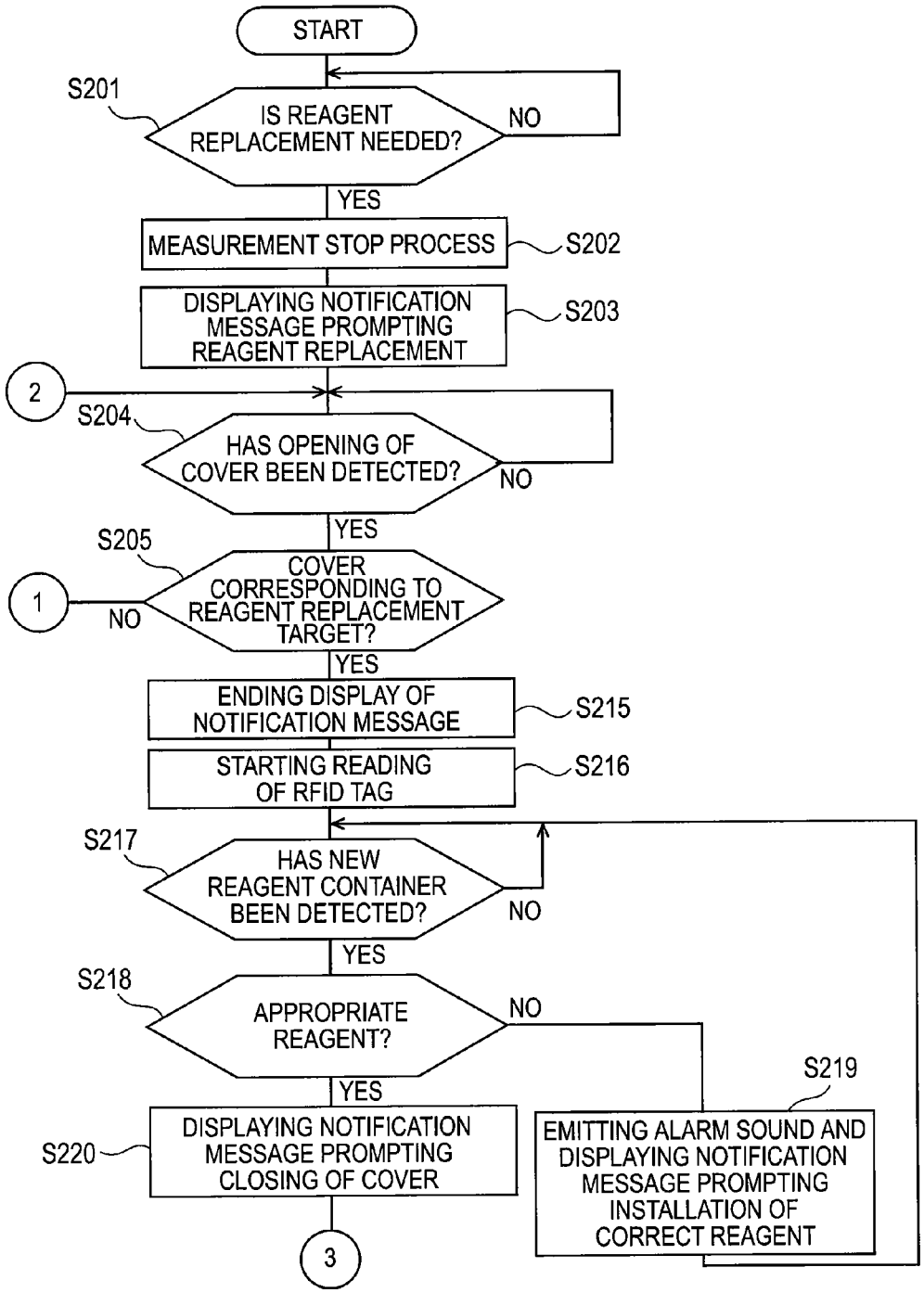

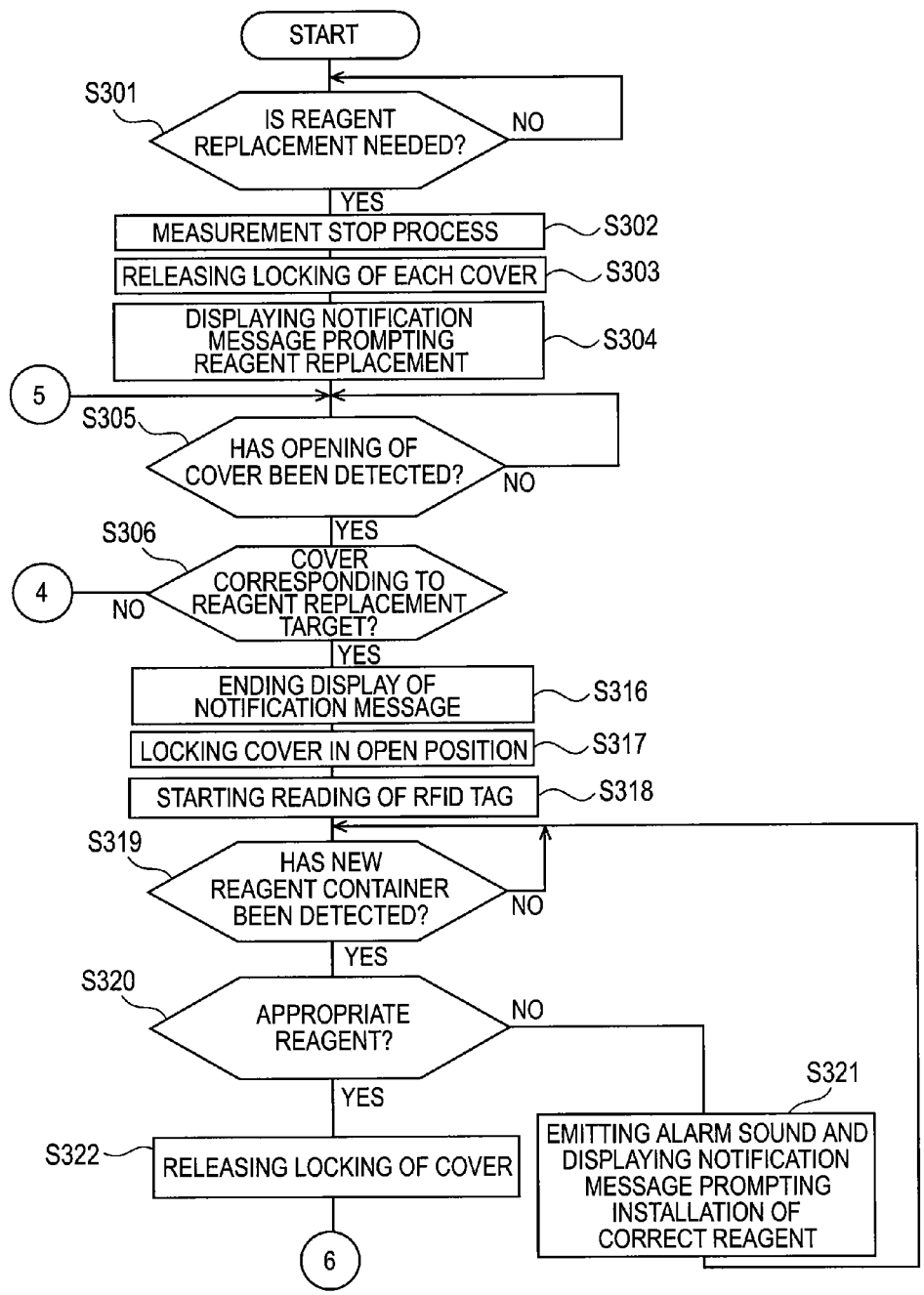

SAMPLE ANALYZER AND METHOD OF NOTIFYING USER BY THE SAME

RELATED APPLICATIONS

This application claims priority under 35 U.S.C. §119 to Japanese Patent Application No. 2010-078995 filed on Mar. 30, 2010, the entire content of which is hereby incorporated by reference.

BACKGROUND OF THE INVENTION

1. Field of the Invention

The present invention relates to a sample analyzer analyzing a sample by using a reagent and a method of notifying a user by the sample analyzer.

2. Background Art

There have been known a sample analyzer in which a plurality of reagent containers can be set. For example, in Japanese Laid-Open Patent Publication No. H10-96733, an automatic analyzer including a reagent bottle storage is disclosed. A plurality of reagent bottles are set in a plurality of set positions within the reagent bottle storage, and indication lamps are provided at the respective set positions. In addition, the automatic sample analyzer is provided with a reagent information reading device. After reagent information was read from a barcode attached to a reagent bottle, an indication lamp which is positioned at the set position on which the reagent bottle is to be set is lit or flashes in order to indicate the location to set the reagent bottle. An operator confirms the set position of the reagent bottle by the indication lamp and then sets the reagent bottle.

However, in the automatic analyzer, even when the indication lamp which is positioned at the set position is lit or flashes, the operator may set the reagent bottle in a wrong position.

SUMMARY OF THE INVENTION

The scope of the present invention is defined solely by the appended claims, and is not affected to any degree by the statements within this summary.

According to a first aspect of the present invention, a sample analyzer comprising:

a first container set section in which a first reagent container containing a first reagent to be used in sample analysis is set, wherein the first container set section includes a first operating section which is operated by a user when setting the first reagent container in the first container set section;

a first detector configured to detect an operation of the first operating section by the user;

a second container set section in which a second reagent container containing a second reagent to be used in sample analysis is set, wherein the second container set section includes a second operating section which is operated by the user when setting the second reagent container in the second container set section;

a second detector configured to detect an operation of the second operating section by the user;

an output section; and a controller configured to control the output section to output a predetermined notification, if the second detector detects the operation of the second operating section by the user when it is required to set the first reagent container in the first container set section.

According to a second aspect of the present invention, a method of notifying a user by a sample analyzer, the method comprising:

determining whether it is required to set a first reagent container in a first container set section and whether it is required to set a second reagent container in a second container set section, wherein the first container set section includes a first operating section which is operated by a user when setting the first reagent container in the first container set section and the second container set section includes a second operating section which is operated by the user when setting the second reagent container in the second container set section; and outputting a predetermined notification by an output section if detecting an operation of the second operating section by the user when it is determined that the first reagent container is required to be set in the first container set section.

BRIEF DESCRIPTION OF THE DRAWINGS

FIG. 13 is a flowchart showing the procedures of a sample analysis control process of the information processing unit according to the first embodiment.

FIG. 14A is a flowchart showing the procedures of a reagent replacement control process of the information processing unit according to the first embodiment.

FIG. 19A is a flowchart showing the procedures of a reagent replacement control process of an information processing unit according to the second embodiment.

DETAILED DESCRIPTION OF THE PREFERRED EMBODIMENTS

Hereinafter, embodiments of the invention will be described on the basis of the drawings.

First Embodiment

[Configuration of Sample Analyzer]

Figure 1:
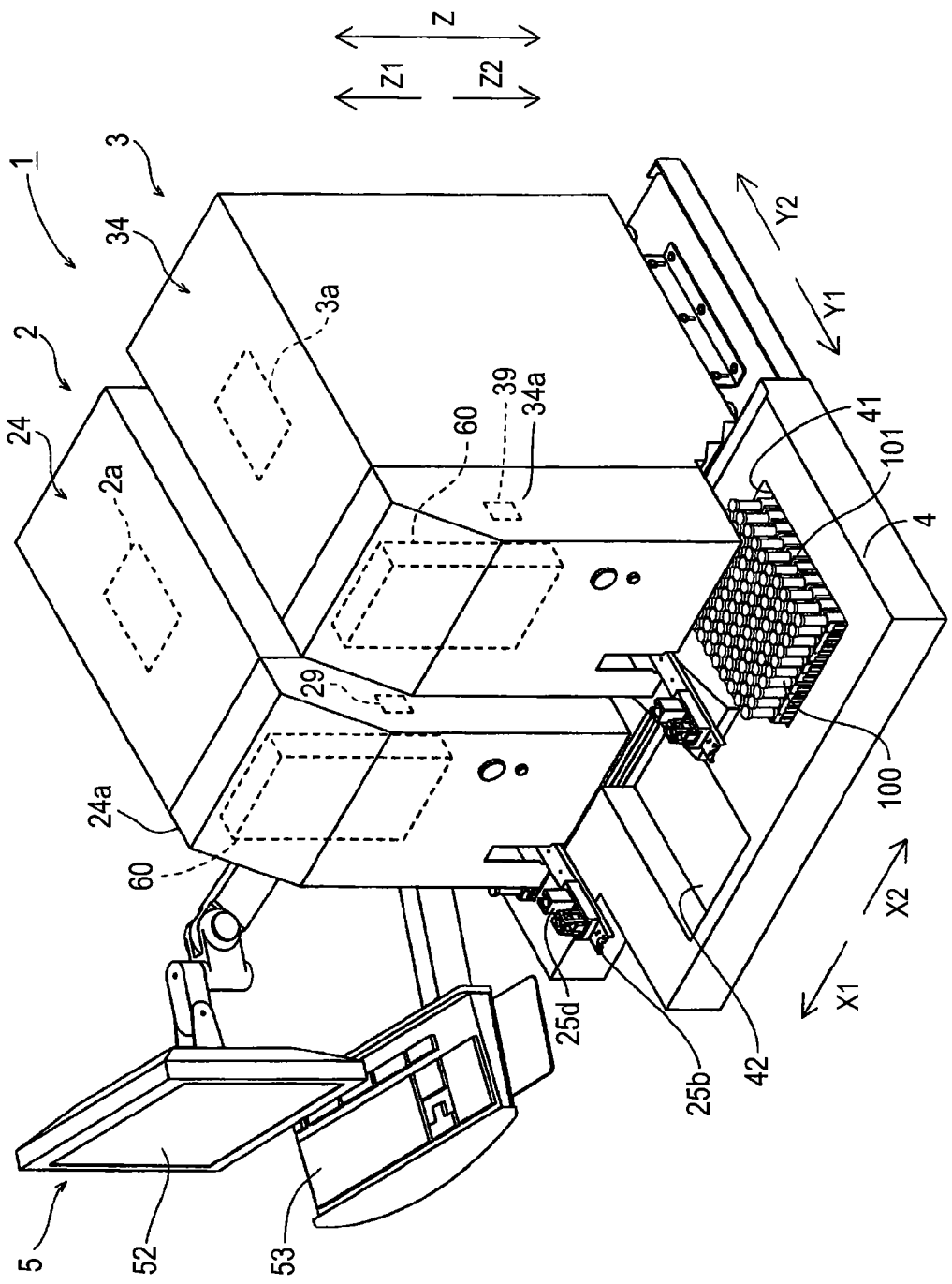
FIG. 1 is a perspective view showing the entire configuration of a sample analyzer according to a first embodiment.

FIG. 1 is a perspective view showing the entire configuration of a sample analyzer according to this embodiment. The sample analyzer 1 according to this embodiment is a multiple blood cell analyzer which classifies blood cells contained in a blood sample into white blood cells, red blood cells, platelets, and the like and counts the number for each kind of blood cell. As shown in FIG. 1, the sample analyzer 1 according to this embodiment includes two measuring units, which are a first measuring unit 3 disposed in the direction of the arrow X2 and a second measuring unit 2 disposed in the direction of the arrow X1, a sample transport unit (sampler) 4 which is disposed in front of the first measuring unit 3 and the second measuring unit 2 (in the direction of the arrow Y1) and an information processing unit 5 which is composed of a personal computer (PC) electrically connected to the first measuring unit 3, the second measuring unit 2, and the sample transport unit 4. In addition, the sample analyzer 1 is connected to a host computer 6 (see FIG. 2) by the information processing unit 5.

<Configuration of Measuring Units]

Figure 2:
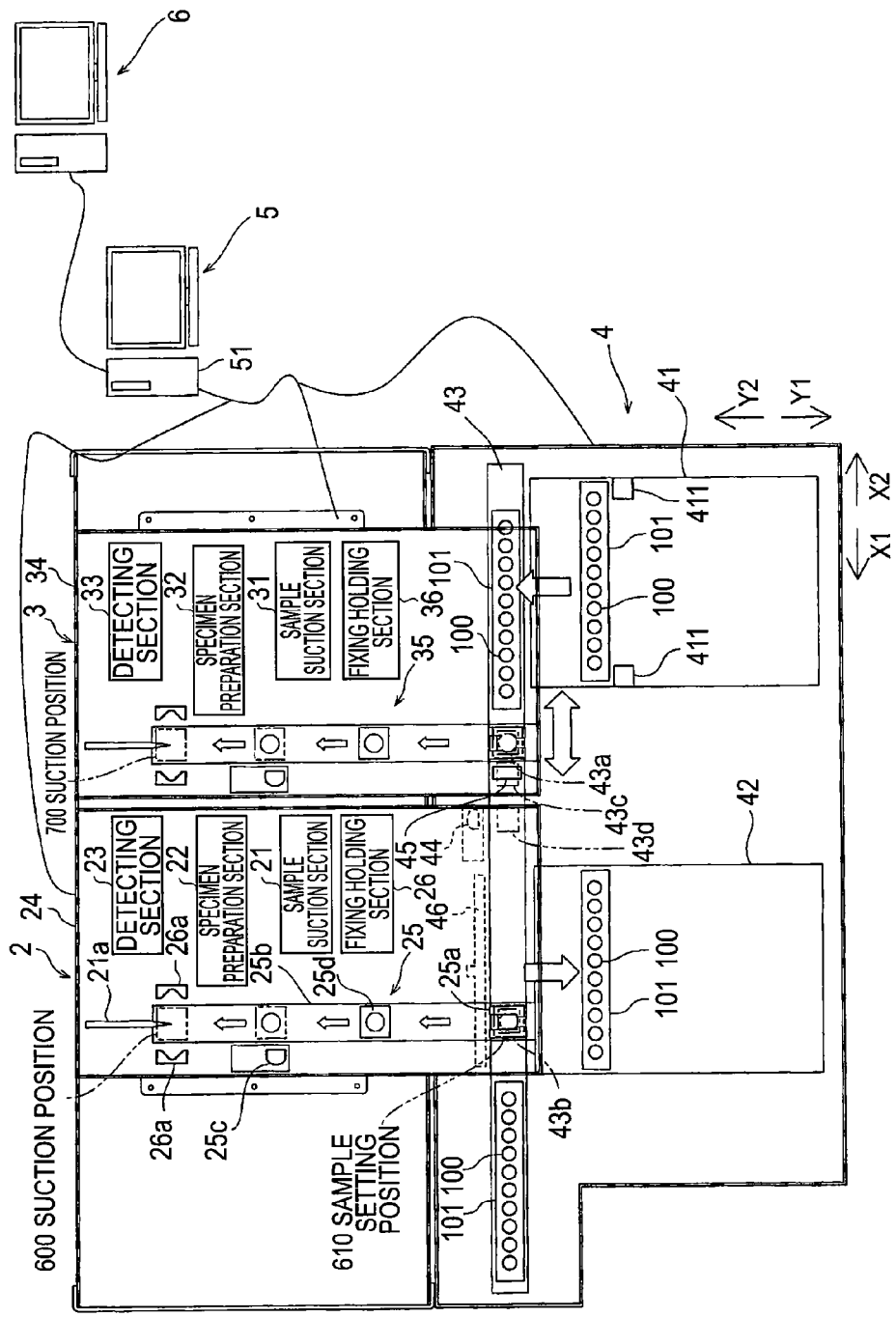
FIG. 2 is a schematic view showing the configuration of the sample analyzer according to the first embodiment.

FIG. 2 is a schematic view showing the configuration of the sample analyzer 1 according to this embodiment. As shown in FIGS. 1 and 2, the first measuring unit 3 and the second measuring unit 2 are substantially the same kind of measuring units and are disposed next to each other. In greater detail, in this embodiment, the second measuring unit 2 uses the same measurement principle as that of the first measuring unit 3 and measures a sample relative to the same measurement item. Further, the second measuring unit 2 also measures a measurement item which is not analyzed by the first measuring unit 3. In addition, as shown in FIG. 2, the second measuring unit 2 and the first measuring unit 3 have sample suction sections 21 and 31 which suction blood which is a sample from a sample container 100, specimen preparation sections 22 and 32 which prepare a measurement specimen from the blood suctioned by the sample suction sections 21 and 31, and detectors 23 and 33 which detect blood cells in the blood from the measurement specimen prepared by the specimen preparation sections 22 and 32, respectively. As shown in FIG. 1, in the first measuring unit 3 and the second measuring unit 2, driver substrates 3a and 2a are provided to drive actuators for the mechanism sections and receive a detection signal from a sensor, respectively.

In addition, as shown in FIG. 2, the second measuring unit 2 and the first measuring unit 3 include unit covers 24 and 34 which accommodate therein the sample suction sections 21 and 31, the specimen preparation sections 22 and 32, and the like, sample container transport sections 25 and 35 which take sample containers 100 into the unit covers 24 and 34 and transport the sample containers 100 up to suction positions 600 and 700 at which the sample suction sections 21 and 31 perform a suction operation, and fixing holding sections 26 and 36 which fix and hold sample containers 100 at the suction positions 600 and 700, respectively. Since the first measuring unit 3 and the second measuring unit 2 are substantially the same kind of measuring units as described above, the second measuring unit 2 will be described hereinbelow and the description for the first measuring unit 3 will be omitted.

Figure 3:
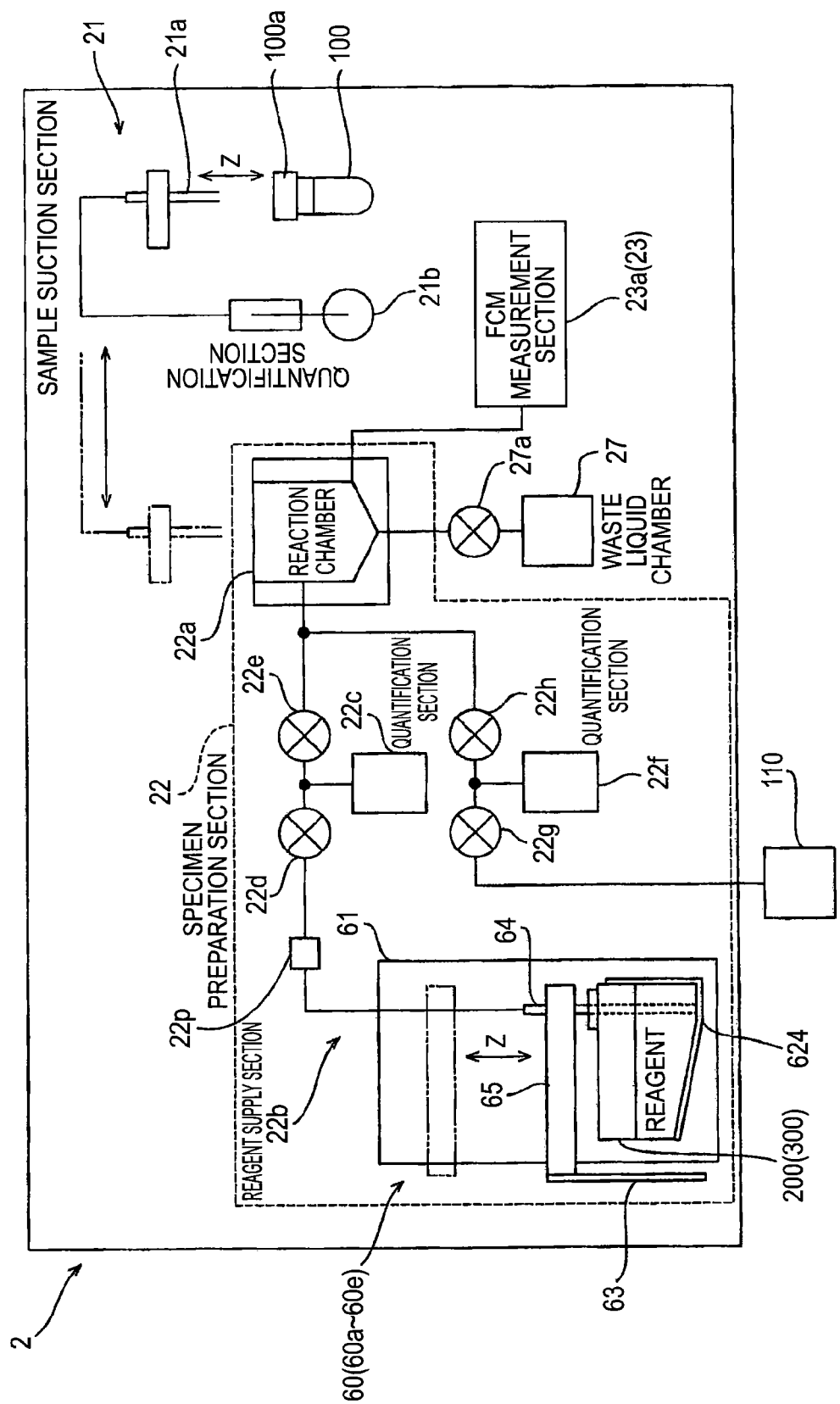
FIG. 3 is a schematic view showing the configuration of a measuring unit according to the first embodiment.

FIG. 3 is a schematic view showing the configuration of the second measuring unit according to this embodiment. As shown in FIG. 3, the sample suction section 21 has a piercer 21a which is a suction tube through which a reagent passes and a quantification section 21b. The piercer 21a is formed so that the tip end thereof can penetrate (puncture) a sealing lid 100a to be described later of a sample container 100. In addition, the piercer 21a is configured to be moved in the vertical direction (Z direction) by a piercer driving section (not shown) and to be moved up to a reaction chamber 22a to be described later. The quantification section 21b is composed of a syringe pump or the like and has a function of suctioning and discharging a predetermined amount of sample from a sample container 100 via the piercer 21a. Accordingly, a predetermined amount of sample necessary for sample measurement is suctioned from a sample container 100 and can be supplied to the reaction chamber 22a.

The detector 23 performs RBC detection (detection of red blood cells) and PLT detection (detection of platelets) by a sheath flow DC detection method and performs HGB detection (detection of hemoglobin in blood) by an SLS-hemoglobin method. In addition, as shown in FIG. 3, the detector 23 has an FCM measurement section 23a which performs WBC detection (detection of white blood cells) by a flow cytometry method using semiconductor laser. The FCM measurement section 23a includes a flow cell through which particles pass, a semiconductor laser which irradiates the particles passing through the flow cell with light, and a light-receiving section which receives scattered light from the particles irradiated with the light. In addition, the detection result obtained by the detector 23 is transmitted to the information processing unit 5 as measurement data (measurement result) of the sample.

As shown in FIG. 3, the specimen preparation section 22 of the second measuring unit 2 has the reaction chamber 22a and a reagent supply section 22b connected to the reaction chamber 22a. The reaction chamber 22a is configured to mix and react a sample (blood) suctioned by the sample suction section 21 and a reagent supplied from the reagent supply section 22b together. A plurality of the reaction chambers 22a is provided in accordance with the kind of measurement. The reaction chambers 22a are each supplied with a plurality of kinds of reagents (staining liquid and the like) according to the measurement items, respectively, and measurement specimens according to the various measurement items are prepared through the sample-reagent mixing and reaction process. The prepared measurement specimen is supplied to the FCM measurement section 23a.

In this embodiment, the reagent supply section 22b is provided in the unit cover 24 and has a reagent container holder 60 which holds a plurality of reagent containers 200 (see FIG. 9) or 300 (see FIG. 10) each containing a predetermined amount of reagent. In such a reagent container holder 60, a piercer 64 is provided to suction the reagent in the reagent container 200 (or 300). In addition, the reagent supply section 22b has a bubble sensor 22p, a quantification section 22c including a syringe pump and a diaphragm pump and electromagnetic valves 22d and 22e which open and close the flow passage when a suctioned reagent is transferred to the quantification section 22c and the reaction chamber 22a. As shown in FIG. 3, the bubble sensor 22p is provided in the flow passage between the piercer 64 and the reaction chamber 22a to detect bubbles which are included in the liquid suctioned from the piercer 64. Further, in addition to the reagent containers 200 (or 300) which are held in the reagent container holder 60, the reagent supply section 22b has a quantification section 22f for transferring reagents (hemolytic agent and the like) from a large capacity reagent container 110, disposed outside the measuring unit, and electromagnetic valves 22g and 22h. The reagent containers 200 and 300 will be described later in detail.

As shown in FIG. 1, an openable and closable front cover 24a is provided on the front side of the unit cover 24. The reagent container holder 60 is disposed in an upper front portion of the second measuring unit 2 and is exposed to the outside by opening the front cover 24a. Accordingly, a user can easily replace the reagent containers 200 and 300. In addition, an openable and closable front cover 34a is also provided on the front side of the unit cover 34 of the first measuring unit 3. Similarly, the reagent container holder 60 is disposed in an upper front portion of the first measuring unit 3 and is exposed to the outside by opening the front cover 34a.

In addition, the first measuring unit 3 and the second measuring unit 2 are provided with buzzers 39 and 29 emitting an alarm sound, respectively. The buzzers 39 and 29 are connected to the driver substrates 3a and 2a, respectively, and emit an alarm sound by a control signal of the information processing unit 5.

Figure 4:
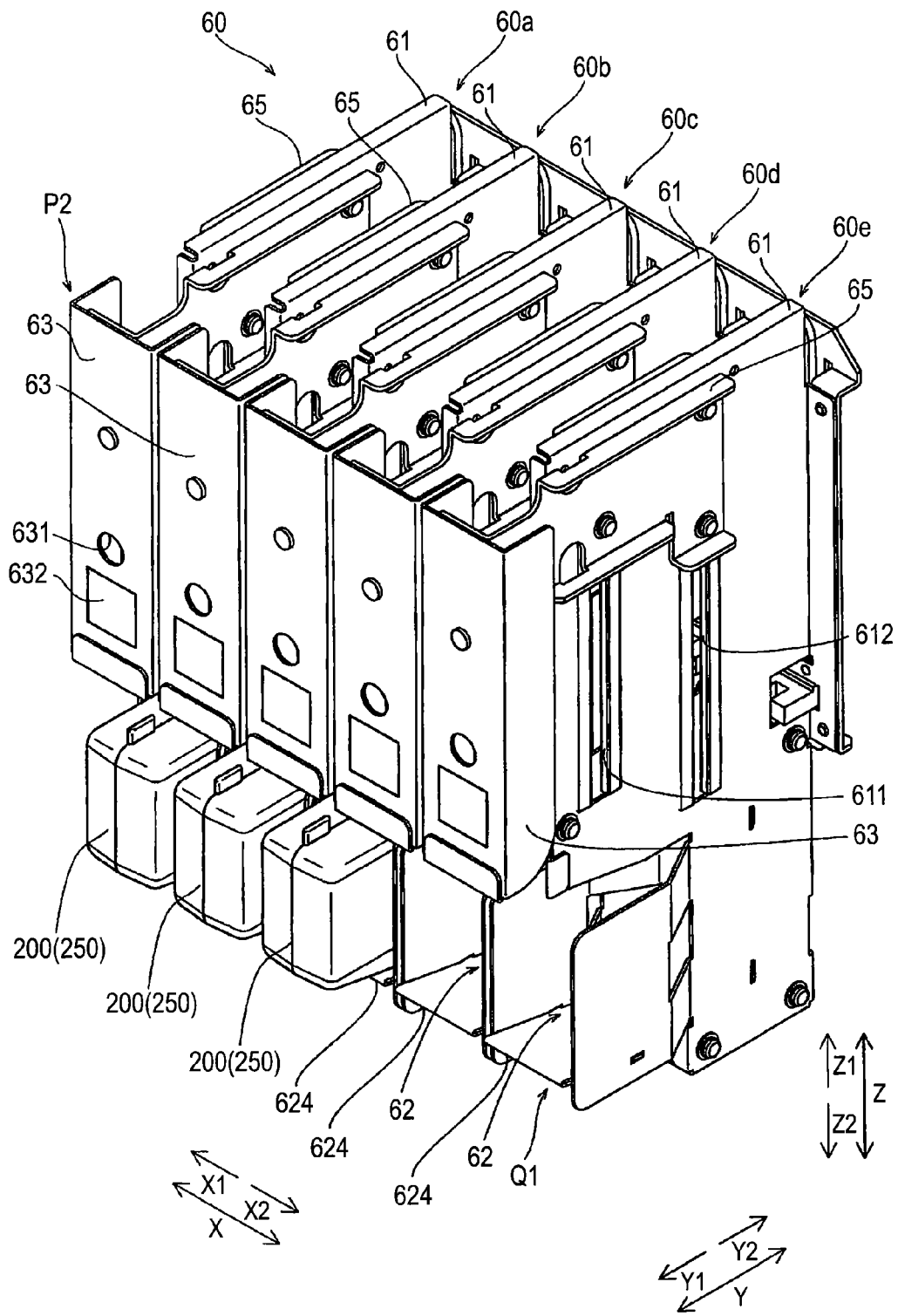
FIG. 4 is a perspective view showing the configuration of a reagent container holder of the measuring unit according to the first embodiment.
Figure 5:
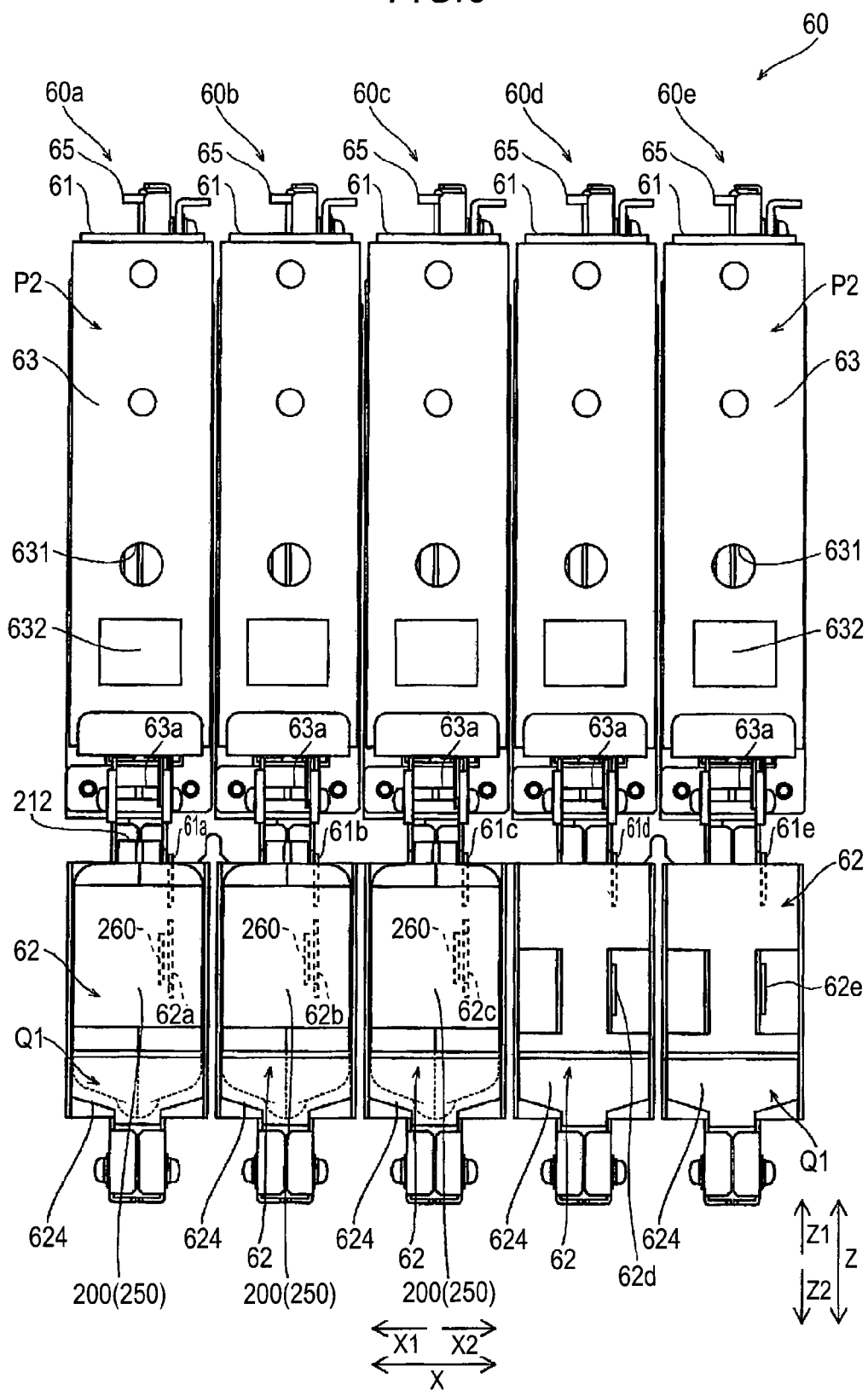
FIG. 5 is a front view showing the configuration of the reagent container holder of the measuring unit according to the first embodiment.

Next, the configuration of the reagent container holder 60 will be described in detail. FIGS. 4 and 5 are a perspective view and a front view showing the configuration of the reagent container holder of the second measuring unit according to this embodiment, respectively. As shown in FIGS. 4 and 5, the reagent container holder 60 has five holder sections 60a, 60b, 60c, 60d, and 60e and is configured to hold a total of five (five kinds) reagent containers 200 (or 300). The reagent containers 200 (or 300) which are held in the reagent container holder 60 contain different kinds of reagents (staining liquid) for measuring a plurality of measurement items by the FCM measuring section 23a, respectively. As the reagent container, the reagent container 200 (see FIG. 9) having a large size (about 100 mL) and the reagent container 300 (see FIG. 10) having a small size (about 20 mL) are used in accordance with the kinds of reagents and the holder sections 60a to 60e are configured to hold any of the reagent containers 200 and 300. That is, the five holder sections 60a to 60e have similar configurations. In the three holder sections 60a to 60c, the reagent containers 200 having a large size are set, and in the two holder sections 60d and 60e, the reagent containers 300 having a small size (not shown in FIGS. 4 and 5) are set. In greater detail, the reagent containers 200 each containing a staining liquid for sub-class classification of white blood cells are installed in the holder sections 60a to 60c. The reagent container 300 containing a staining liquid for detection of reticulocytes is installed in the holder section 60d and the reagent container 300 containing a staining liquid for detection of platelets is installed in the holder section 60e. Each of the holder sections 60a to 60e has a chassis 61, a reagent container installation section 62, a cover 63 for opening and closing the reagent container installation section 62, the above-described piercer 64, and a piercer lifting mechanism 65.

In the holder sections 60a to 60e, radio frequency identification (RFID) readers 61a to 61e and antennas 62a to 62e which are connected to the RFID readers 61a to 61e, respectively, in association therewith are provided. In each of the reagent containers 200 and 300, an RFID tag 260 (360) is attached which stores various information related to the reagent. The RFID tags 260 (360) are passive tags not needing a battery and are driven by radio waves sent from the antennas 62a to 62e. The RFID tag 260 (360) stores information such as a reagent code indicating the kind of the reagent, an expiration date of the reagent, the maximum number of uses of the reagent, a serial number individually assigned to each reagent, a lot number and an expiry date after opening. When reading reagent information from the RFID tag 260 (360), the RFID readers 61a to 61e send radio waves from the antennas 62a to 62e. When the radio waves are sent from the antennas 62a to 62e, they are partially reflected by the RFID tag 260 (360). The reagent information stored in the RFID tag 260 (360) is put on the reflected wave. The antennas 62a to 62e receive the reflected wave from the RFID tag 260 (360) and the RFID readers 61a to 61e obtain the reagent information included in this reflected wave.

The reagent container installation section 62 is provided in the lower portion of the chassis 61 (see FIG. 5) and has an inner space which is provided for installing a reagent container 200 (300).

Figure 6:
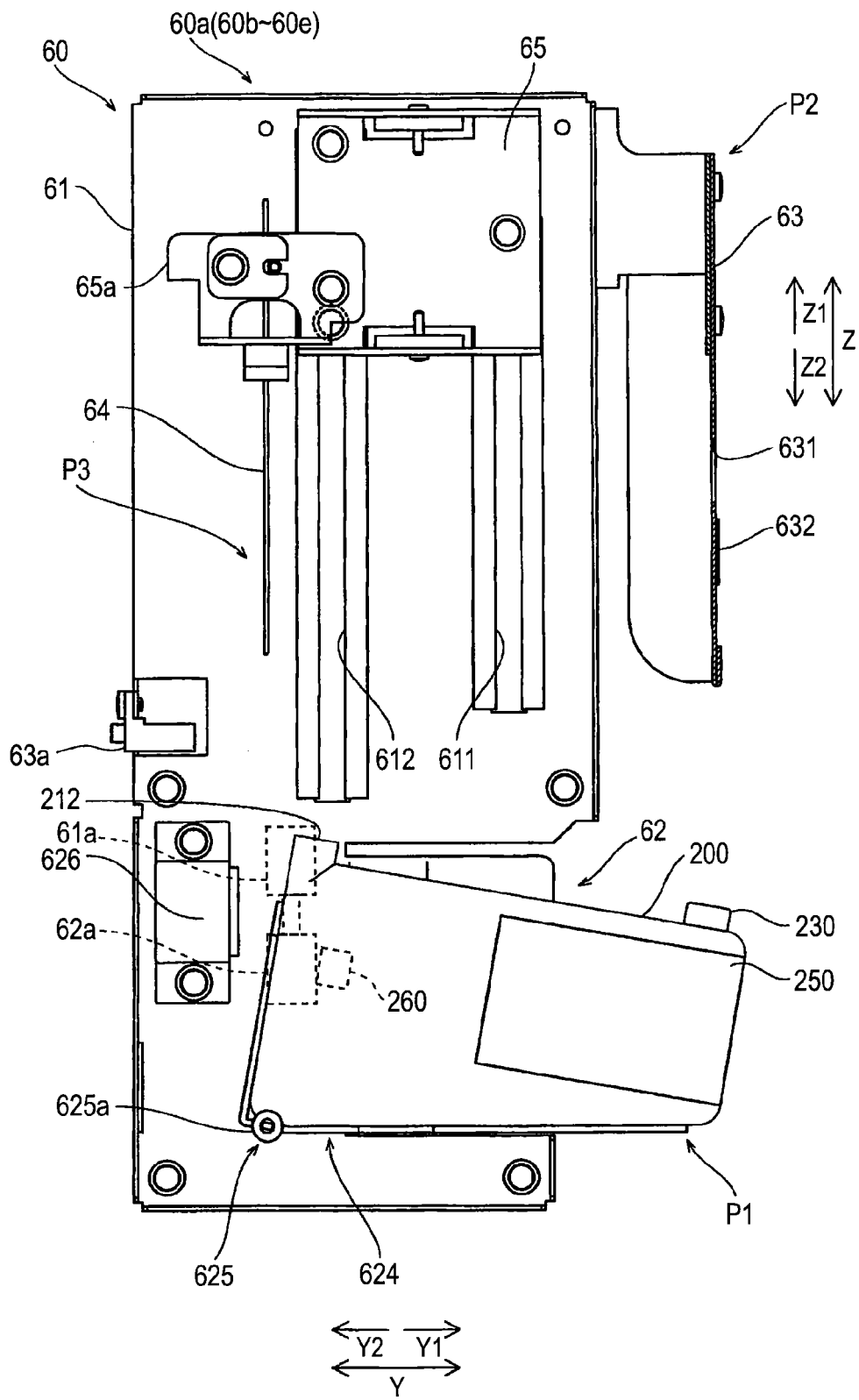
FIG. 6 is a vertical cross-sectional view showing the internal configuration of the reagent container holder according to the first embodiment.
Figure 7:
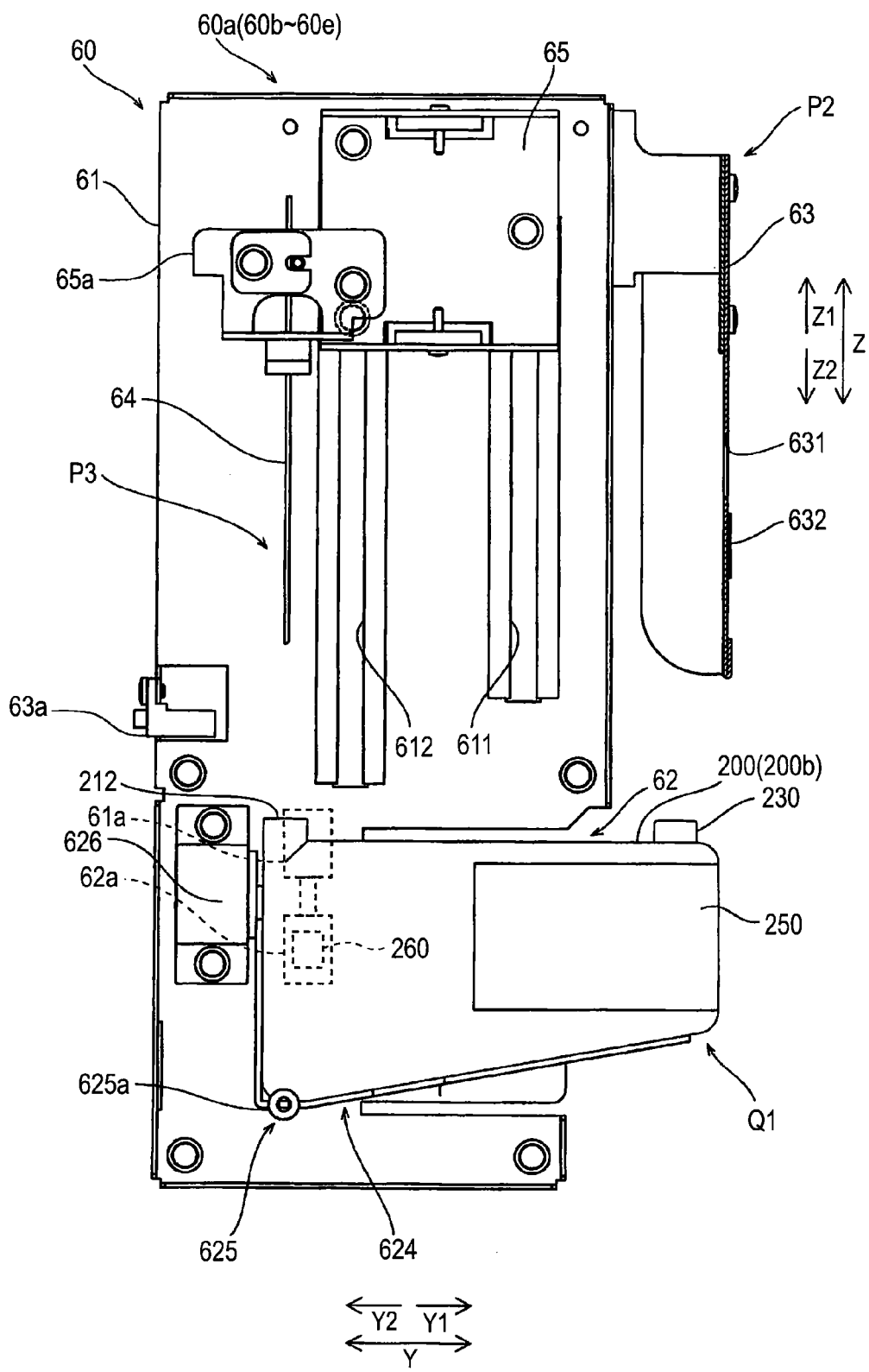
FIG. 7 is a vertical cross-sectional view showing the internal configuration of the reagent container holder according to the first embodiment.
Figure 8:
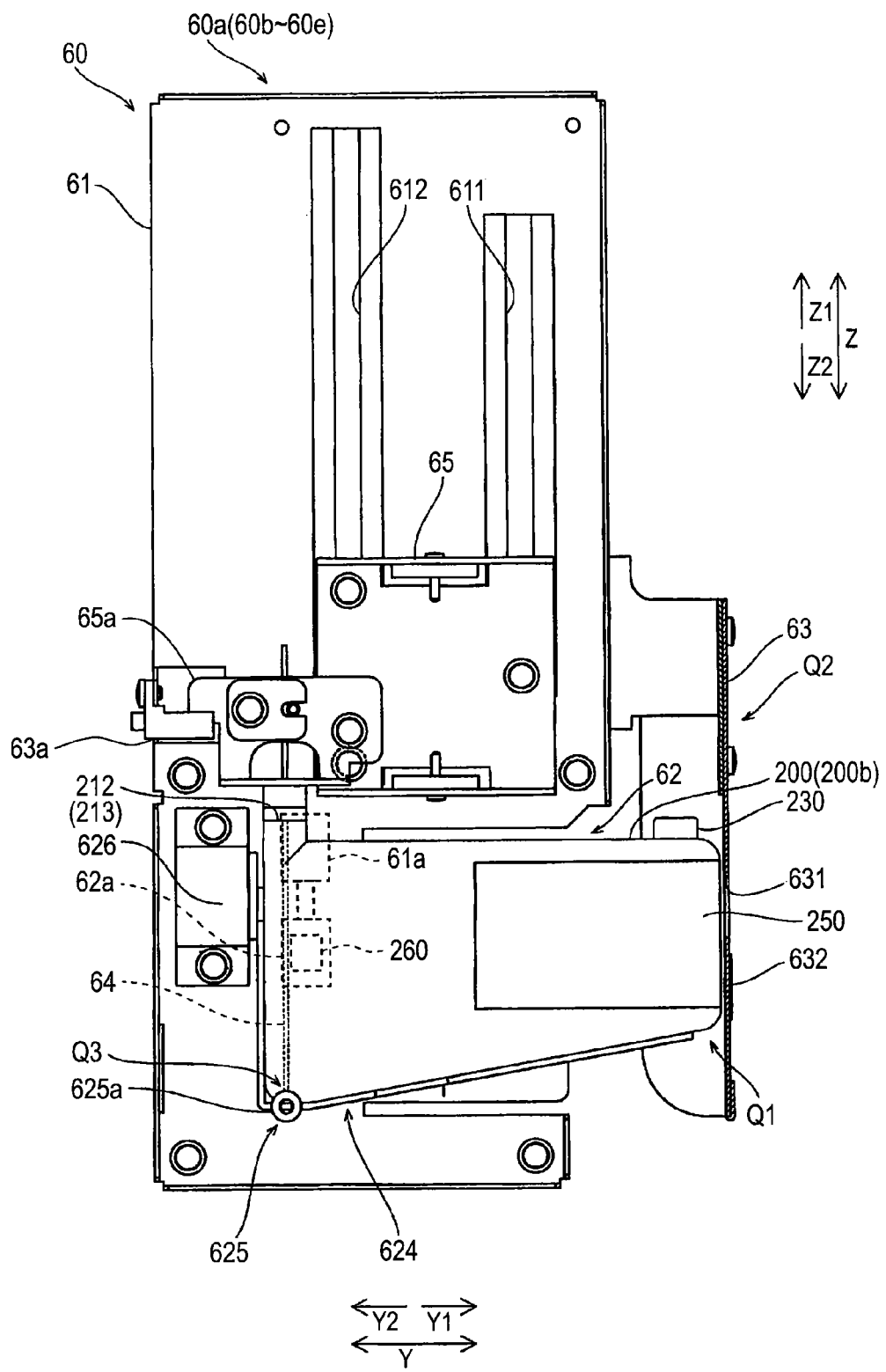
FIG. 8 is a vertical cross-sectional view showing the internal configuration of the reagent container holder according to the first embodiment.

FIGS. 6 to 8 are vertical cross-sectional views schematically showing the internal configuration of the reagent container holder according to this embodiment. FIG. 6 shows a state in which a reagent container is attached or removed in the reagent container holder. FIG. 7 shows a state in which a reagent container is set in the reagent container holder. FIG. 8 shows a state in which the cover of the reagent container holder is lowered. As shown in FIG. 6, the reagent container installation section 62 has a support section 624 which supports a reagent container 200 (300) and a rotation mechanism 625 which rotatably supports the support section 624. The support section 624 is formed to have a shape corresponding to the shape of a reagent container 200 (300) and is brought into contact with the front and lower surfaces of the reagent container 200 (300). The rotation mechanism 625 is configured to rotate the support section 624 around a bearing 625a provided near the bent portion of the support section 624.

Further, in the chassis 61, a holding section 626 is provided which holds the rotating support section 624 through the contact with the support section 624. The holding section 626 is provided with a magnet and holds the front portion of the support section 624 using a magnetic force. Accordingly, the support section 624 is configured to move between an installation position P1 (see FIG. 6) on which the lower surface of a reagent container 200 (300) is made horizontal and a setting position Q1 (see FIG. 7) at which the front and rear end surfaces of a reagent container 200 (300) are made vertical. An opening section 212 (312) to be described later of a reagent container 200 (300) is made horizontal and is positioned immediately below the piercer 64 in a state in which the reagent container is disposed at this setting position Q1 as shown in FIG. 7.

Each of the antennas 62a to 62e is attached to the side portion of each reagent container installation section 62.

When a reagent container 200 (300) is positioned at the setting position Q1, the RFID tag 260 (360) of the reagent container 200 (300) is disposed next to the antennas 62a to 62e in the reagent container installation section 62 in which the reagent container 200 (300) is installed. Accordingly, the reflected wave from the RFID tag 260 (360) of the reagent container 200 (300) installed in the reagent container installation section 62 is received by the nearest of the antennas 62a to 62e (that is, the one disposed next to the tag). The reflected wave sent from the RFID tag 260 (360) is very weak and is not received by the other antennas other than the nearest antenna.

As shown in FIG. 6, the cover 63 is disposed on the front side of each of the holder sections 60a to 60e (chassis 61) (in the direction of the arrow Y1) and is attached to the piercer lifting mechanism 65. The cover 63 is configured to be moved between a lifting position P2 (see FIG. 7) related to opening of the reagent container installation section 62 and a lowered position Q2 (see FIG. 8) related to covering (closing) of the reagent container installation section 62 by the piercer lifting mechanism 65. In addition, as shown in FIG. 5, a window section 631 composed of an opening is provided at a predetermined position in the cover 63. As shown in FIG. 8, in a state in which the cover 63 is positioned at the lowered position Q2 related to covering (closing) of the reagent container installation section 62, a user can visually confirm a label 250 (350, see FIG. 10) adhered to the reagent container 200 (300) via this window section 631. A mark for identifying the kind of the reagent container 200 (300) (kind of the reagent) is printed at a position which can be visually confirmed via the window section 631 on the label 250 (350). In addition, a label 632, on which a mark is printed for identifying the kind of the reagent container 200 (300) (kind of the reagent) set in the reagent container installation section 62, is adhered to the cover 63. That is, in the five holder sections 60a to 60e, reagent containers 200 (300) each containing a fixed kind of reagent are set, and thus in accordance with this, the labels 632 for identifying the kinds of the reagents to be set are adhered to the covers 63 of the holder sections 60a to 60e, respectively. Accordingly, in a state in which the reagent containers 200 (300) are set in the reagent container installation section 62 (in a state in which the cover 63 is lowered to the lowered position Q2), it is possible to confirm whether the correct reagents are set in the holder sections 60a to 60e from the labels 632 which are adhered to the covers 63 and the labels 250 (350) which are visually confirmed via the window sections 631.

In addition, each of the holder sections 60a to 60e is provided with a cover opening/closing sensor 63a which detects the opening and closing of the corresponding cover 63. The cover opening/closing sensor 63a is a photo-interrupter which has a light-emitting section and a light-receiving section opposed to each other and detects the opening and closing of the cover by detecting a detecting piece 65a provided in the piercer lifting mechanism 65. In greater detail, when the cover is at the lowered position Q2, the detecting piece 65a is disposed between the light-emitting section and the light-receiving section of the cover opening/closing sensor 63a, and when the light-receiving section detects that the detecting piece 65a shields the light from the light-emitting section, the closure of the cover 63 is detected. When the light-receiving section detects the light from the light-emitting section without the shielding by the detecting piece 65a, the opening of the cover 63 is detected.

As shown in FIG. 7, the piercer 64 is disposed above the innermost portion (end in the direction of the arrow Y2) of the reagent container installation section 62 and is configured to be moved in the vertical direction (Z direction) by the piercer lifting mechanism 65 holding the piercer 64. The piercer 64 is sharply formed so that the tip end thereof can penetrate (puncture) a sealing material 213 (313) (see FIGS. 9 and 10) for closing the opening section 212 (312) of the reagent container 200 (300). In addition, as shown in FIG. 3, the upper end of the piercer 64 is connected to the flow passage (omitted in FIGS. 6 to 11) extending to the reaction chamber 22a and the quantification section 22c.

As shown in FIGS. 7 and 8, the piercer lifting mechanism 65 is configured to hold the piercer 64 and the cover 63. In addition, the piercer lifting mechanism 65 is provided to be moved in the vertical direction (Z direction) to groove sections 611 and 612 provided in the chassis 61. Accordingly, the piercer lifting mechanism 65 is configured to integrally move the piercer 64 in the vertical direction (Z direction) in conjunction with the opening and closing (lifting and lowering) of the cover 63. In addition, as shown in FIG. 7, in a state in which the cover 63 is disposed at the lifting position P2, the piercer 64 is disposed at a lifting position P3 above the reagent container installation section 62. In addition, as shown in FIG. 8, in a state in which the cover 63 is disposed at the lowered position Q2, the piercer 64 is disposed at a lowered position Q3 near the inner bottom portion immediately below the opening section 212 (312) of the reagent container 200 (300).

As shown in FIG. 3, the quantification section 22c is configured to suction a predetermined amount of reagent in a reagent container 200 (300) to the inside of the quantification section 22c via the piercer 64 by opening the electromagnetic valve 22d and closing the electromagnetic valve 22e in a state in which the piercer 64 is disposed at the lowered position Q3 in the reagent container 200 (300) (see FIG. 8). Accordingly, the reagent is quantified in a predetermined amount necessary for the preparation of a measurement specimen. In addition, the quantification section 22c is configured to transfer the reagent quantified in the quantification section 22c to the reaction chamber 22a by closing the electromagnetic valve 22d and opening the electromagnetic valve 22e.

In addition, the quantification section 22f and the electromagnetic valves 22g and 22h which are connected to the large capacity reagent container 110 externally disposed are configured in the same manner. By controlling the operations of these sections, various reagents are transferred to the inside of the reaction chamber 22a. In addition, in the second measuring unit 2, a waste liquid chamber 27 is provided for discarding a specimen on which the measurement has been performed (on which the preparation has been performed), and is configured to discard a specimen on which the measurement has been performed (on which the preparation has been performed) by opening and closing of an electromagnetic valve 27a.

As shown in FIG. 2, the sample container transport section 25 is configured to be linearly moved in the vertical direction (in the direction of the arrows Z1 and Z2) and has a hand section 25a capable of gripping a sample container 100, a sample container transfer section 25b horizontally moving a sample container 100 in the direction of the arrows Y1 and Y2 and a barcode reading section 25c.

The hand section 25a is disposed above a transport passage for a rack 101 which is transported by the sample transport unit 4. In addition, the hand section 25a is configured to move downward (in the direction of the arrow Z2) and then grip a sample container 100 accommodated in the rack 101 when the sample transport unit 4 transports the sample container 100 to a predetermined intake position 43b.

In addition, the hand section 25a can stir the blood in the gripped sample container 100. In addition, after stirring, the hand section sets the sample container 100 in a sample setting section 25d which is moved to a sample setting position 610 by the sample container transfer section 25b. As shown in FIG. 2, the second intake position 43b and the sample setting position 610 are disposed to overlap each other in a planar view.

The sample container transfer section 25b has the sample setting section 25d as shown in FIGS. 1 and 2 and can move the sample setting section 25d to a predetermined position according to the operation of the measurement process. In greater detail, the sample setting section 25d can be disposed at the suction position 600 and the sample setting position 610 shown in FIG. 2 by the sample container transfer section 25b. In addition, as shown in FIG. 1, the sample container transfer section 25b is configured to be moved to a predetermined position which is outside the unit cover 24 so that a user can manually set a sample container 100 when an emergency sample is measured or the sample transport unit 4 is not used.

The barcode reading section 25c is configured to read a barcode (not shown) adhered to each sample container 100. The barcode (not shown) of each sample container 100 is adhered uniquely to each sample and is used in the management of the analysis results of the samples and the like.

The fixing holding section 26 is configured to fix and hold a sample container 100 transferred to the suction position 600. In greater detail, as shown in FIG. 2, the fixing holding section 26 has a pair of chucks 26a and is configured to grip a sample container 100 by moving the pair of chucks 26a to be close to each other.

Next, the reagent containers 200 and 300 will be described in detail which are used in the second measuring unit 2 and the first measuring unit 3 according to this embodiment and are set in the reagent container holders 60.

Figure 9:
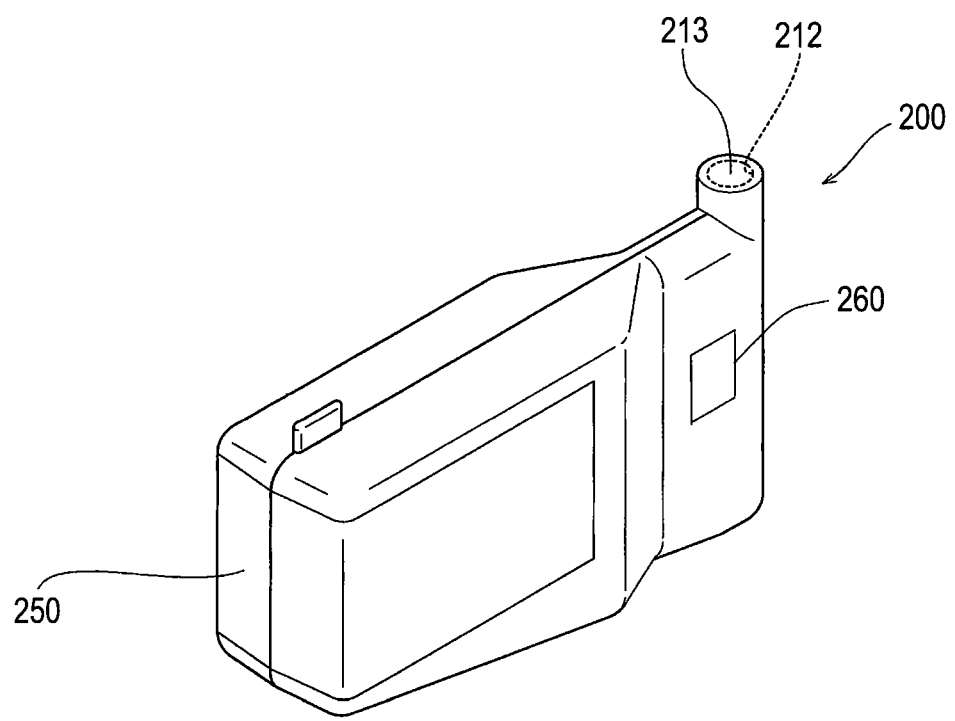
FIG. 9 is a perspective view showing the configuration of a reagent container according to the first embodiment.
Figure 10:
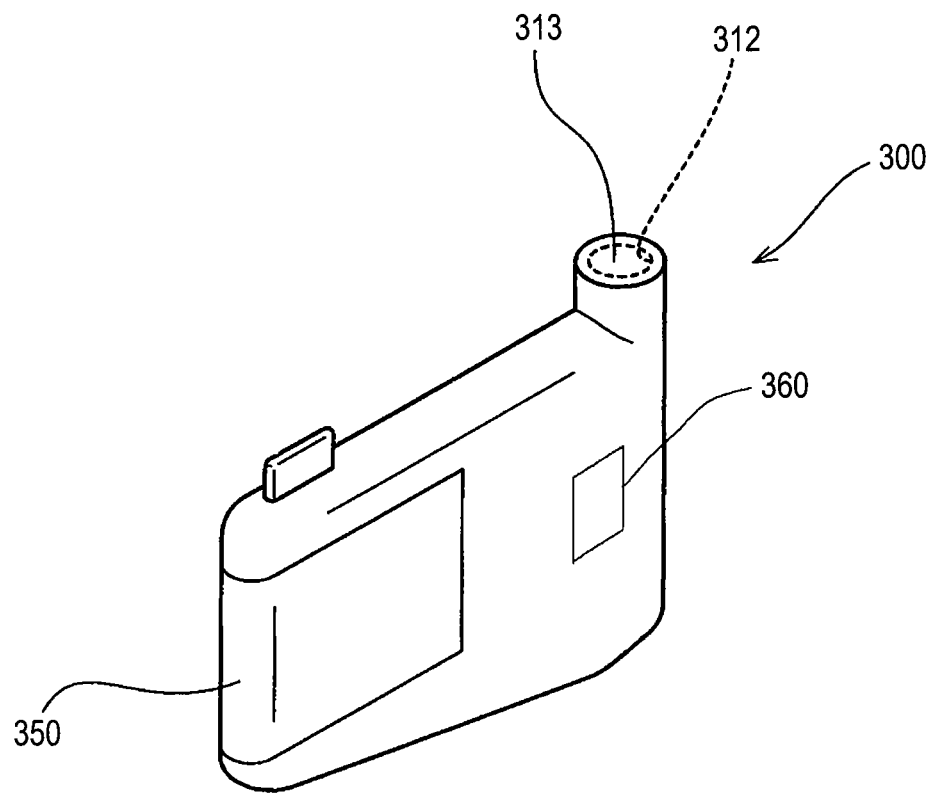
FIG. 10 is a perspective view showing the configuration of a reagent container according to the first embodiment.

FIGS. 9 and 10 are perspective views each showing the configuration of a reagent container according to this embodiment. In this embodiment, as shown in FIGS. 9 and 10, the reagent containers 200 having a large size (capacity about 100 mL) and the reagent containers 300 having a small size (capacity about 20 mL) are used in accordance with the kind of reagent to be contained. That is, the reagent containers 200 having a large size contain a staining liquid for sub-class classification of white blood cells and the reagent containers 300 having a small size contain a staining liquid for detection of reticulocytes and a staining liquid for detection of platelets. The reagent containers 200 and 300 have the opening sections 212 and 312, into which the piercer 64 is inserted, at the upper portion of the front end (end in the insertion direction when being inserted into the reagent container installation section 62), and the front portions in which the opening sections 212 and 312 are provided, respectively, have the same shape. In addition, the rear portion (opposite portion to the front side at which the opening section 212 is provided) of the reagent container 200 having a large size have a large width. The reagent container 300 having a small size is formed to have a uniform width over the entire length. In this manner, since the front portions of the reagent containers 200 and 300 have a common shape, the reagent containers can be set in the reagent container installation sections 62 of the holder sections 60a to 60e having the same shape, respectively. Further, as shown in FIGS. 9 and 10, the RFID tags 260 and 360 are respectively attached to the corresponding portions in the side surfaces of the front portions of both of the reagent container 200 having a large size and the reagent container 300 having a small size. The front portions of the reagent containers 200 and 300 have the same shape. Accordingly, in a state in which the reagent containers 200 and 300 are installed in the reagent container installation section 62, the RFID tags 260 and 360 provided in any of the reagent containers 200 and 300 are disposed at positions next to the corresponding antennas 62a to 62e, respectively.

As shown in FIGS. 9 and 10, the opening section 212 (312) is formed in a cylindrical shape from the front portions of the reagent containers 200 and 300 to the upper side. The opening section 212 (312) is provided with a sealing material 213 (313) made of aluminum foil to close the reagent container 200 (300). As described above, when the cover 63 is closed and the piercer 64 is lowered in conjunction with the closure in a state in which the reagent containers 200 and 300 are installed in the reagent container installation section 62, the sealing materials 213 and 313 are punctured by the tip end of the piercer 64 and the piercer 64 is inserted into the opening sections 212 and 312.

In addition, as shown in FIGS. 9 and 10, the label 250 (350), on which the name of the contained reagent, the lot number of the reagent, the expiration date, and the like are printed, is adhered to each reagent container 200 (300). This label 250 (350) is adhered over the rear side surface and at least one of the lateral side surfaces of each reagent container 200 (300). In addition, the label 250 (350) is partially (portion corresponding to the rear side surface of each reagent container 200 (300)) or entirely colored with a color indicating the kind of the reagent contained and thus the kind of the reagent can be identified with the color displayed in the label 250 (350). It can be confirmed whether the reagent container 200 (300) is set in the correct one of holder sections 60a to 60e depending on whether the color of this label 250 (350) matches the color of the label 632 (see FIG. 5) adhered to the cover 63 of the reagent container holder 60.

<Configuration of Sample Transport Unit>

As shown in FIGS. 1 and 2, the sample transport unit 4 has a pre-analysis rack holding section 41 which can hold a plurality of racks 101 accommodating sample containers 100 each containing a sample before analysis, a post-analysis rack holding section 42 which can hold a plurality of racks 101 accommodating sample containers 100 each containing a sample after analysis, a rack transport section 43 which horizontally and linearly moves racks 101 in the direction of the arrows X1 and X2, a barcode reading section 44, a presence detection sensor 45 which detects the presence or absence of a sample container 100 and a rack output section 46 which moves racks 101 in the post-analysis rack holding section 42.

The pre-analysis rack holding section 41 has a rack input section 411 and is configured to push the racks 101 held in the pre-analysis rack holding section 41 onto the rack transport section 43 one by one due to the movement of the rack input section 411 in the direction of the arrow Y2.

As shown in FIG. 2, the rack transport section 43 is configured so that due to the transport of a rack 101, predetermined sample containers 100 held in the rack are arranged at an intake position 43a at which the first measuring unit 3 takes a sample and the intake position 43b at which the second measuring unit 2 takes a sample. In addition, the rack transport section 43 is configured to transport sample containers 100 to a sample detection position 43c at which the presence detection sensor 45 confirms the presence or absence of a sample container 100 and a reading position 43d at which the barcode reading section 44 reads the barcode (not shown) (see FIG. 4) of a sample container 100.

The rack output section 46 is disposed to be opposed to the post-analysis rack holding section 42 with the rack transport section 43 interposed therebetween and is configured to horizontally move in the direction of the arrow Y1. In addition, the rack output section 46 is configured to push a rack 101 disposed at a position between the rack output section 46 and the post-analysis rack holding section 42 of the rack transport section 43 to the post-analysis rack holding section 42 due to the horizontal movement in the direction of the arrow Y1.
<Configuration of Information Processing Unit>

Figure 11:
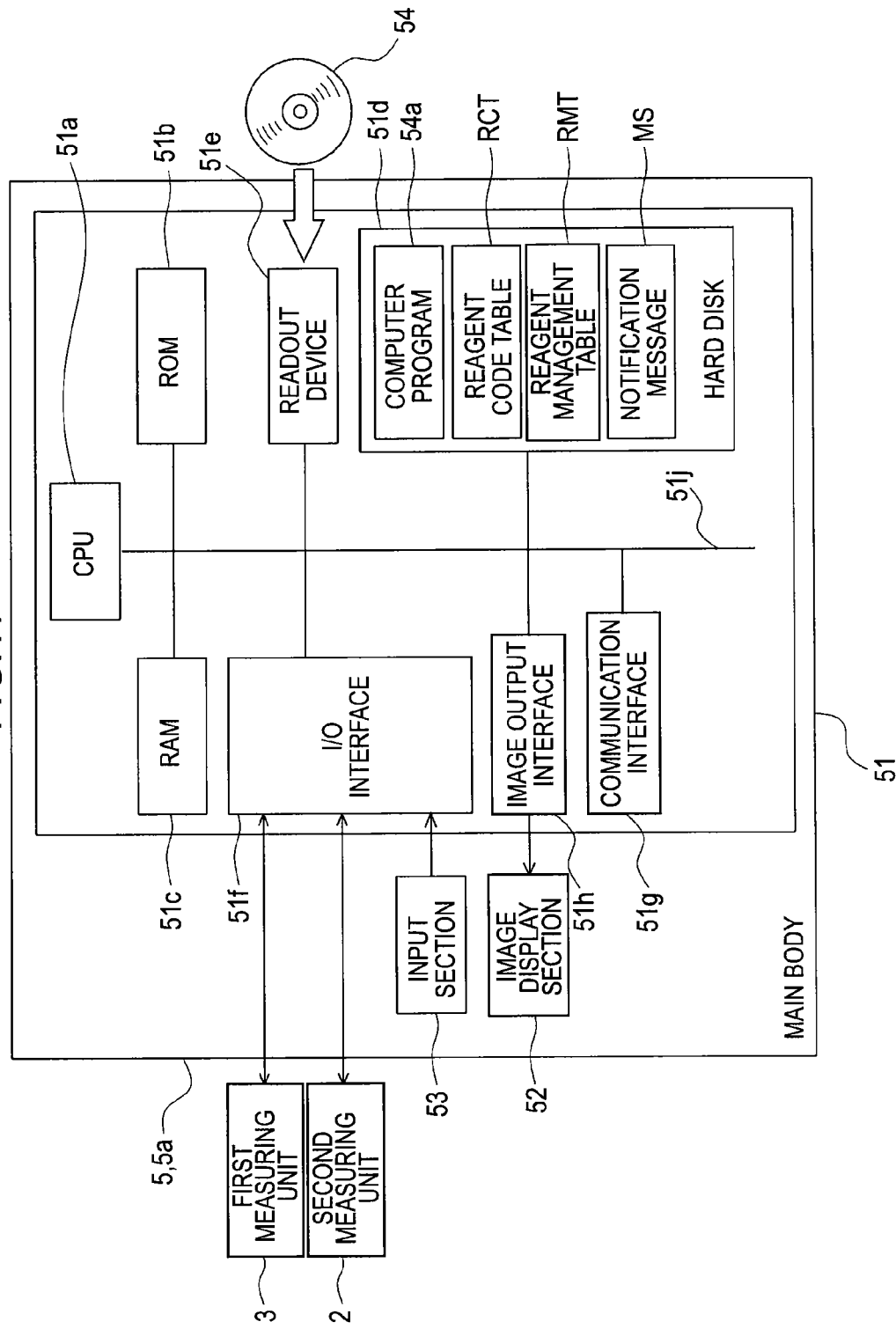
FIG. 11 is a block diagram showing the configuration of an information processing unit according to the first embodiment.

Next, the configuration of the information processing unit 5 will be described. The information processing unit 5 is composed of a computer. FIG. 11 is a block diagram showing the configuration of the information processing unit 5. The information processing unit 5 is realized by a computer 5a. As shown in FIG. 11, the computer 5a includes a main body 51, an image display section 52, and an input section 53. The main body 51 includes a CPU 51a, a ROM 51b, a RAM 51c, a hard disk 51d, a readout device 51e, an I/O interface 51f, a communication interface 51g, and an image output interface 51h. The CPU 51a, the ROM 51b, the RAM 51c, the hard disk 51d, the readout device 51e, the I/O interface 51f, the communication interface 51g, and the image output interface 51h are connected to each other by a bus 51j.

The readout device 51e reads out from a portable recording medium 54 a computer program 54a for prompting the computer to function as the information processing unit 5 and can install the computer program 54a on the hard disk 51d.

Figure 12:
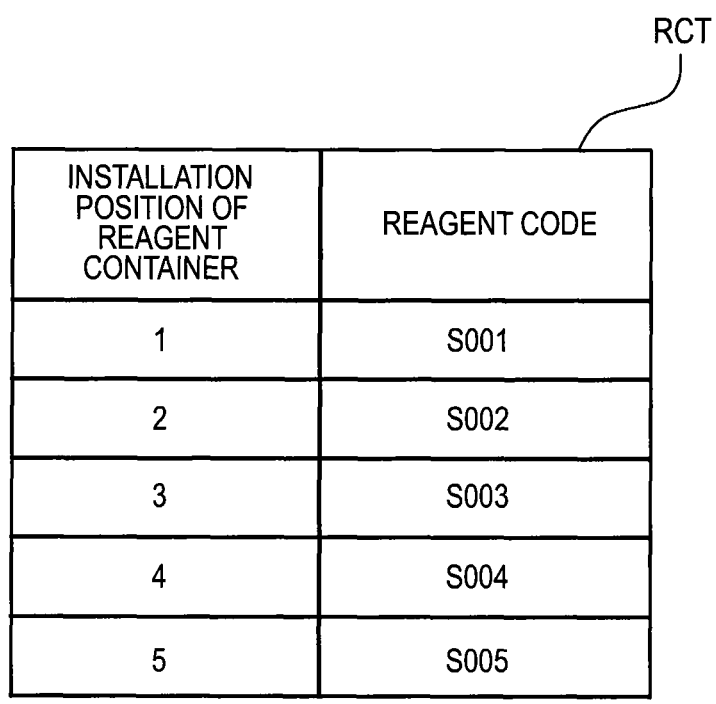
FIG. 12 is a schematic view showing the structure of a reagent code table according to the first embodiment.

In the hard disk 51d, a reagent code table RCT is stored in which information designating the holder sections 60a to 60e and reagent codes indicating the kinds of the reagents which can be installed in the holder sections 60a to 60e are stored in association with each other. FIG. 12 is a schematic view showing the structure of the reagent code table. As described above, for each of the holder sections 60a to 60e, the kind of the reagent which can be installed is decided. That is, in the holder section 60a, a reagent container is installed containing a staining liquid for first sub-class classification of white blood cells, in the holder section 60b, a reagent container is installed containing a staining liquid for second sub-class classification of white blood cells, in the holder section 60c, a reagent container is installed containing a staining liquid for third sub-class classification of white blood cells, in the holder section 60d, a reagent container is installed containing a staining liquid for detection of reticulocytes, and in the holder section 60e, a reagent container is installed containing a staining liquid for detection of platelets. In the reagent code table RCT, a reagent code "S001" of the staining liquid for first sub-class classification of white blood cells is stored in association with a reagent installation position number "1" indicating the holder section 60a, a reagent code "S002" of the staining liquid for second sub-class classification of white blood cells is stored in association with a reagent installation position number "2" indicating the holder section 60b, a reagent code "S003" of the staining liquid for third sub-class classification of white blood cells is stored in association with a reagent installation position number "3" indicating the holder section 60c, a reagent code "S004" of the staining liquid for detection of reticulocytes is stored in association with a reagent installation position number "4" indicating the holder section 60d, and a reagent code "S005" of the staining liquid for detection of platelets is stored in association with a reagent installation position number "5" indicating the holder section 60e.

In addition, in the hard disk 51d, an area of a reagent management table RMT is provided. The reagent management table RMT is a table for managing the reagents which are installed in the reagent container holder 60 and stores information such as an installation position (holder section) of the reagent, a reagent code, an expiration date of the reagent, the maximum number of uses of the reagent, a serial number, a lot number, an expiry date after opening, and opening date and the number of uses.

Further, in the hard disk 51d, notification messages MS are stored. The notification messages MS are text information which is output when the reagent replacement is needed or a user replaces the reagent. In greater detail, in the hard disk 51d, various notification messages MS are stored such as "There is no reagent. Please open the cover and replace the reagent container.", "A cover not corresponding to the replacement target has been opened. Please close the cover.", "Please set an appropriate reagent container.", "The appropriate reagent container has been set. Please close the cover." and "The reagent replacement has been completed."

Each of the first measuring unit 3 and the second measuring unit 2 are connected to the I/O interface 51f via a cable. The I/O interface 51f is connected to the driver substrates 3a and 2a of the first measuring unit 3 and the second measuring unit 2 so as to communicate therewith and can output a control signal to the driver substrates 3a and 2a. Such driver substrates 3a and 2a receiving the control signal decode this control signal and drive the actuators for the mechanism sections in accordance with the control signal. In addition, the bubble sensor 22p, the five cover opening/closing sensors 63a and the RFID readers 61a to 61e are connected to the driver substrates 3a and 2a, and signals which are output from the bubble sensor 22p, the five cover opening/closing sensors 63a and the RFID readers 61a to 61e are transmitted to the information processing unit 5 via the driver substrates 3a and 2a.

[Operation of Sample Analyzer]

Hereinafter, the operation of the sample analyzer 1 according to this embodiment will be described.

<Sample Analysis Operation>

First, the sample analysis operation of the sample analyzer 1 will be described. The sample analysis is performed when the CPU 51a of the information processing unit 5 executes a sample analysis control process and thus controls the first measuring unit 3, the second measuring unit 2 and the sample transport unit 4. FIG. 13 is a flowchart showing the procedures of the sample analysis control process of the information processing unit 5. When starting the sample analysis using the sample analyzer 1, a user operates the information processing unit 5 to give a sample analysis start instruction to the sample analyzer 1. The CPU 51a awaits the reception of such a sample analysis start instruction (NO in Step S101), and when receiving the sample analysis start instruction (YES in Step S101), the CPU prompts the sample transport unit 4 to transport a rack 101 (Step S102), prompts the barcode reading section 25c to read the barcode adhered to a first sample container 100 (on the farthest downstream side in the transport direction in the rack 101), and obtains sample information (sample ID, measurement order, patient information, and the like) of the sample (Step S103). From this sample information, the CPU 51a decides the measuring unit for performing the measurement of the sample from between the first measuring unit 3 and the second measuring unit 2 (Step S104), takes the sample container 100 into the decided measuring unit and suctions the sample from the sample container 100 to the sample suction section 21 or 31 (Step S105). The sample container 100 in which the suctioning of the sample has been completed is discharged from the measuring unit and is returned to the original position in the rack 101.

After the suctioning of the sample, the CPU 51a prompts the specimen preparation section 22 to mix the sample and a reagent according to a measurement item of the sample and prepares a measurement specimen (Step S106). In this manner, when the measurement specimen is prepared by using the reagent once, the CPU 51a updates the number uses of the reagent to a value increased by one in the reagent management table RMT. Further, the CPU 51a prompts the specimen preparation section 22 to supply the measurement specimen to the detector 23 and prompts the detector 23 to measure the sample (Step S107). The CPU 51a obtains the measurement data of the sample, analyzes this measurement data and obtains the analysis result of the sample (Step S108). Next, the CPU 51a determines whether all the sample containers 100 held in the rack 101 have been supplied to the measuring unit (Step S109). When there is a sample container 100 which is not yet supplied to the measuring unit (NO in Step S109), the CPU returns the process to Step S102, transports the rack 101 and prompts the barcode reading section 25c to read the barcode adhered to the subsequent sample container 100 to obtain sample information of the sample. After that, the processes after Step S105 are executed to analyze the sample.

In Step S109, when all the sample containers 100 are supplied to the measuring unit (YES in Step S109), the CPU 51a prompts the sample transport unit 4 to transport the rack 101 up to the post-analysis rack holding section 42 (Step S110) and determines whether there is a subsequent rack 101 accommodating sample containers 100 on which the measurement has not yet been performed (Step S111). When there is a subsequent rack 101 (YES in Step S111), the CPU 51a returns the process to Step S102 and executes the processes after Step S102 on the samples which are held in the subsequent rack 101. Accordingly, a plurality of the racks 101 is continuously transported and the samples which are held in these racks 101 are sequentially analyzed. When there is no subsequent rack 101 accommodating sample containers 100 on which the measurement has not yet been performed (NO in Step S111), the CPU 51a returns the process to Step S101.

In addition, here, the automatic sample analysis operation in which the rack 101 is transported by the sample transport unit 4 has been described, but in the sample analyzer 1, a manual sample analysis operation may also be executed in which a user sets the sample containers 100 one by one without using the sample transport unit 4 and takes the set sample containers 100 into the measuring unit to analyze the samples.

<Reagent Replacement Operation>

Figure 14B:
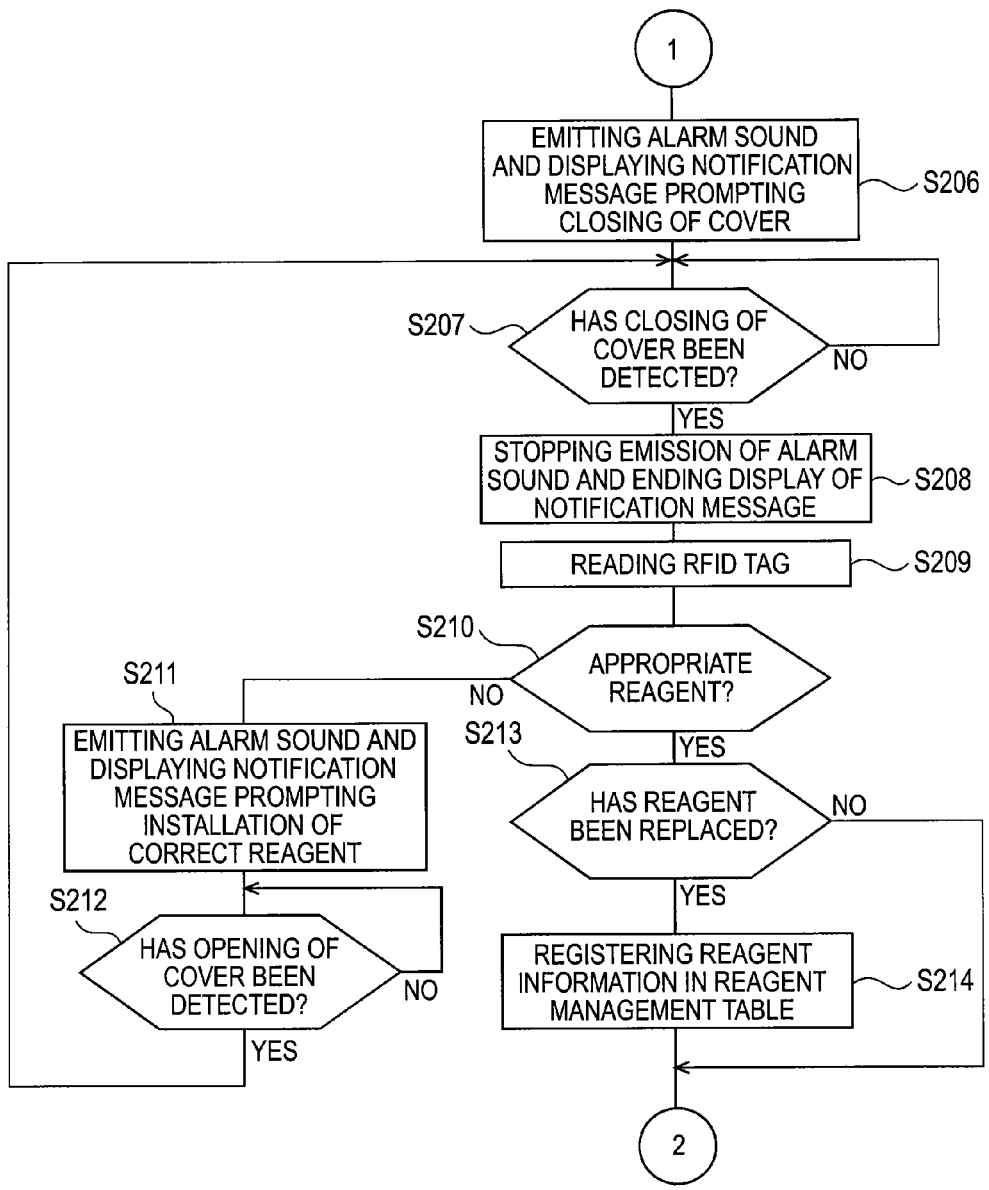
FIG. 14B is a flowchart showing the procedures of the reagent replacement control process of the information processing unit according to the first embodiment.
Figure 14C:
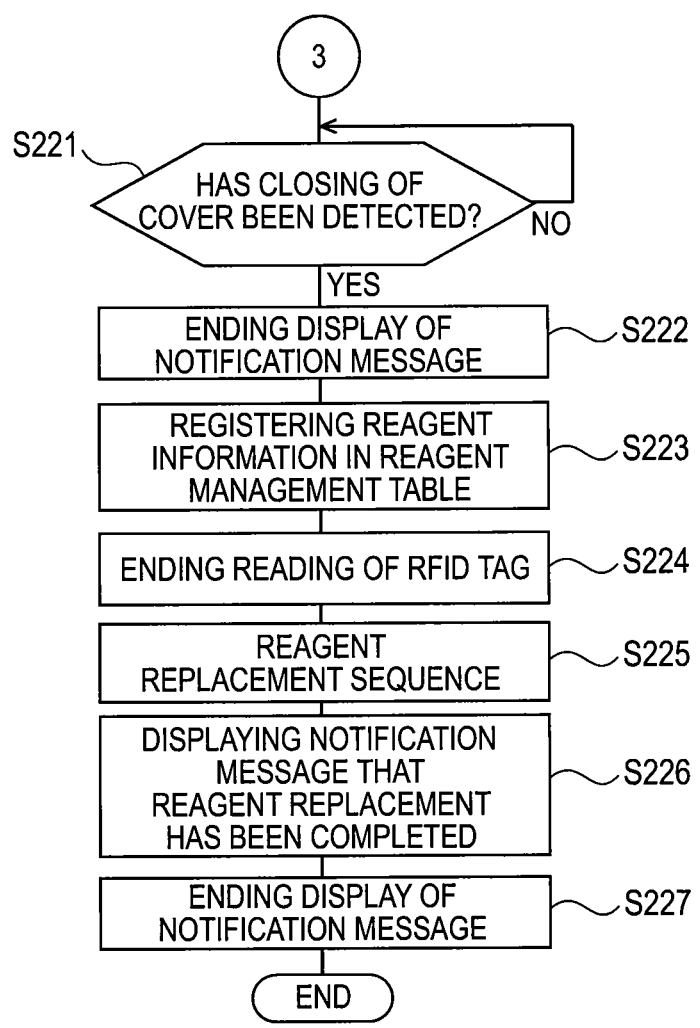
FIG. 14C is a flowchart showing the procedures of the reagent replacement control process of the information processing unit according to the first embodiment.

When the reagent is consumed as a result of the above-described sample analysis or when the expiration date of the reagent has expired, it is required to replace the reagent. In the sample analyzer 1 according to this embodiment, the CPU 51a of the information processing unit 5 executes a reagent replacement control process to control the first measuring unit 3 or the second measuring unit 2, and thus reagent replacement is performed. FIGS. 14A to 14C are flowcharts showing the procedures of the reagent replacement control process of the information processing unit 5 according to this embodiment. First, the CPU 51a determines whether the reagent replacement is needed (Step S201). In this process, when the reagent is consumed due to the analysis and the number of uses of the reagent matches the maximum number of uses in the reagent management table RMT, that is, when the remaining reagent runs out, the reagent replacement is determined to be needed. In addition, also in the case in which the bubble sensor 22p detects bubbles in the reagent which is supplied to the reaction chamber 22a from the reagent container 200 or 300, it is determined that the remaining reagent runs out and the reagent replacement is needed. Further, also in the case in which the expiration date of the reagent has expired or the case in which the expiry date after opening which is decided by an opening date of the reagent has expired, the reagent replacement is determined to be needed.

When the reagent replacement is not needed in Step S201 (NO in Step S201), the CPU 51a repeats the process of Step S201 until the reagent replacement is needed. On the other hand, when the reagent replacement is determined to be needed (YES in Step S201), the CPU 51a executes a measurement stop process of the first measuring unit 3 or the second measuring unit 2 (Step S202). When the automatic sample analysis operation is executed, this measurement stop process is a process of controlling the first measuring unit 3 or the second measuring unit 2 so that the measurement for a sample on which the measurement has not yet been performed does not start and a sample during the measurement at that time is measured until the end. When the manual sample analysis operation is executed, this measurement stop process is a process of controlling the first measuring unit 3 or the second measuring unit 2 so that a sample during the measurement at that time is measured until the end and a new sample is not received. When the measurement stop process is executed, the CPU 51a reads out a notification message MS from the hard disk 51d and displays the notification message "There is no reagent. Please open the cover and replace the reagent container." on the image display section 52 (Step S203). In addition, in Step S203, the CPU 51a emits an alarm sound from the buzzer 29 or 39 in accordance with the above-described notification message.

In Step S203, in accordance with the above-described notification message, the image display section 52 displays the name of the reagent to be replaced and information which shows the measuring unit requiring the replacement of the reagent. The information to be displayed which shows the measuring unit requiring the replacement of the reagent may be, for example, text information such as a name of the first measuring unit 3 or the second measuring unit 2, a unit number, "right measuring unit" or "left measuring unit". Otherwise, image information may be used in which pictures of the first measuring unit 3 and the second measuring unit 2 are displayed and the measuring unit requiring the reagent replacement is displayed with a color different from that of the measuring unit not requiring the reagent replacement. Both of the text information and the image information may be combined.

By such a notification message, a user knows the kind of the reagent to be replaced and the measuring unit requiring the reagent replacement in addition to the information that the reagent replacement is needed. The user prepares a new reagent for replacement and opens the front cover 24a or 34a of the measuring unit requiring the reagent replacement. The user checks the labels 632 adhered to the respective covers 63 of the regent container holder 60, designates the holder section corresponding to a reagent replacement target from among the holder sections 60a to 60e and opens the cover 63 of the holder section corresponding to the reagent replacement target. Thus, a reagent container installation operation is executed. In this manner, when the cover 63 is opened, the cover opening/closing sensor 63a corresponding to the cover 63 detects the opening of the cover 63, that is, detects the reagent container installation operation, and outputs a detection signal. Through the detection signal of the cover opening/closing sensor 63a, the CPU 51a determines whether the opening of any of the covers 63 has been detected (Step S204). When the opening of the cover 63 is not detected (NO in Step S204), the CPU 51a repeats the process of Step S204 until the opening of any of the covers 63 is detected.

On the other hand, when the opening of any of the covers 63 is detected in Step S204 (YES in Step S204), the CPU 51a determines whether the opened cover 63 is a cover of the holder section corresponding to the reagent replacement target (Step S205). When the opened cover 63 is different from the cover of the holder section corresponding to the reagent replacement target (NO in Step S205), the CPU 51a reads out a notification message MS from the hard disk 51*d*, displays the notification message "A cover not corresponding to the replacement target has been opened. Please close the cover." on the image display section 52 and prompts the buzzer 39 or 29 to emit an alarm sound (Step S206). Accordingly, the user is notified of the opening of the cover of the holder section not corresponding to the reagent replacement target and is warned.

When the user closes the opened cover 63, the cover opening/closing sensor 63*a* corresponding to this cover detects the closing of the cover. The CPU 51*a* determines whether the cover 63 has been closed by an output signal of the cover opening/closing sensor 63*a* (Step S207). When the closing of the cover 63 is not detected (NO in Step S207), the CPU 51*a* repeats the process of Step S207 until the closing of the cover 63 is detected.

On the other hand, when the closing of the cover 63 is detected in Step S207 (YES in Step S207), the CPU 51*a* prompts the buzzer 39 or 29 to stop emission of the alarm sound and ends the display of the notification message (Step S208). At this time, the notification message that the display is ending is a notification message which is displayed in Step S206 and prompts the closing of the cover, and the display of the notification message which is displayed in Step S203 and prompts the replacement of the reagent is maintained. At this time, the display of this notification message ends when a notification message, which is displayed in Step S211 to be described later, prompting the installation of an appropriate reagent is displayed.

Here, in the holder section of which the cover 63 has been opened once, the reagent container may be replaced. For example, a reagent other than the reagent which is a replacement target may be replaced because the amount remaining of the reagent is small or the expiration date is close. In addition, it is also considered that the user opens the cover 63 of another holder section different from the holder section corresponding to the reagent which is a replacement target and replaces a reagent container therein with a new reagent container which is a replacement target. Accordingly, the CPU 51*a* drives the RFID reader of the holder section in which the cover 63 is closed, reads out reagent information from the RFID tag 260 of the reagent container 200 or the RFID tag 360 of the reagent container 300, either of which is installed in the above holder section (Step S209) and determines whether the appropriate reagent is installed (Step S210). In this process, the CPU 51*a* reads out a reagent code corresponding to the holder section in which the cover 63 is opened from the reagent code table RCT, and through the determination whether the read reagent code matches the reagent code which is included in the reagent information read out from the RFID tag 260 or 360, it is determined whether the reagent container installed in the holder section is appropriate.

In Step S210, when the replaced reagent is not appropriate (NO in Step S210), the CPU 51*a* reads out a notification message MS from the hard disk 51*d*, displays the notification message "Please set an appropriate reagent container." on the image display section 52 and prompts the buzzer 39 or 29 to emit an alarm sound (Step S211). Accordingly, the user is notified of the fact that the inappropriate reagent has been installed in the holder section and the installation of an appropriate reagent is prompted. Further, the CPU 51*a* determines once again whether the opening of the cover 63 is detected by a detection signal of the cover opening/closing sensor 63*a* (Step S212). When the opening of the cover 63 is not detected (NO in Step S212), the CPU 51*a* repeats the process of Step S212 until the opening of the cover 63 is detected.

On the other hand, when the opening of the cover 63 is detected in Step S212 (YES in Step S212), the CPU 51*a* returns the process to Step S207 and determines whether the cover 63 is closed.

In Step S210, when the appropriate reagent is installed in the holder section in which the cover 63 is closed, that is, when the reagent code of the reagent installed in the holder section matches the reagent code associated with the above holder section (YES in Step S210), the CPU 51*a* determines whether the reagent has been replaced in the holder section (Step S213). In the reagent management table RMT, information related to the installed reagents is registered and unique serial numbers of the reagents are included. That is, when the serial number read from the RFID tag 260 or 360 matches the serial number of the reagent in the installation position, which is registered in the reagent management table RMT, it can be determined that the reagent installed in the above holder section before the opening and closing of the cover 63 is the same as the reagent installed in the above holder section after the opening and closing of the cover 63 and the reagent has not been replaced. On the other hand, when the serial number read out from the RFID tag 260 or 360 does not match the serial number of the reagent in the installation position, which is registered in the reagent management table RMT, it can be determined that the reagent installed in the holder section before the opening and closing of the cover 63 is different from the reagent installed in the holder section after the opening and closing of the cover 63 and the reagent has been replaced. In the process of Step S213, the CPU 51*a* matches the serial number of the reagent read out from the RFID tag 260 or 360 to the serial number of the reagent in the installation position, which is registered in the reagent management table RMT, to determine whether the reagent has been replaced.

In Step S213, when the reagent has been replaced in the holder section (YES in Step S213), the CPU 51*a* stores the reagent information read out from the RFID tag 360 or 260 in association with the installation position indicating the above holder section in the reagent management table RMT (Step S214). In this case, the reagent information corresponding to the installation position which has been stored in the reagent management table RMT, that is, the reagent information related to the reagent before the replacement is deleted. The CPU 51*a* executes the process of Step S214 and then returns the process to Step S204. On the other hand, in Step S213, when the reagent has not been replaced in the holder section (NO in Step S213), the CPU 51*a* returns the process to Step S204.

In Step S205, when the opened cover 63 is a cover of the holder section corresponding to the reagent replacement target (YES in Step S205), the CPU 51*a* ends the display of the notification message prompting the replacement of the reagent, which is displayed in Step S203 (Step S215).

Next, the CPU 51*a* drives the RFID reader of the holder section in which the cover 63 is opened and starts the reading of the reagent information from the RFID tag 260 of the reagent container 200 or the RFID tag 360 of the reagent container 300, either of which is installed in the above holder section (Step S216). In this process, the RFID reader is driven and transmission of the electric wave from the antenna connected to this RFID reader is started. Here, when the reagent container 300 or 200 is replaced in the holder section, the RFID reader reads out reagent information from the RFID tag 360 adhered to a new reagent container 300 or the RFID tag 260 adhered to a new reagent container 200. The CPU 51*a* determines whether a new reagent container has been installed on the basis of the reagent information read out as described above (Step S217). In this process, the CPU 51*a* matches the serial number of the reagent read out from the RFID tag 260 or 360 to the serial number of the reagent in the installation position, which is registered in the reagent management table RMT. When both of them match, the CPU determines that a new reagent container has not been installed, and when both of them do not match, the CPU determines that a new reagent container has been installed. When the installation of a new reagent container is not detected in Step S217 (NO in Step S217), the CPU 51*a* repeats the process of Step S217 until the installation of a new reagent container is detected.

On the other hand, in Step S217, when the installation of a new reagent container is detected (YES in Step S217), the CPU 51*a* determines whether the replaced reagent is appropriate (Step S218). Since the process of Step S218 is the same as the process of Step S210, the description thereof will be omitted.

In Step S218, when the replaced reagent is not appropriate (NO in Step S218), the CPU 51*a* reads out a notification message MS from the hard disk 51*d*, displays the notification message "Please set an appropriate reagent container." on the image display section 52, prompts the buzzer 39 or 29 to emit an alarm sound (Step S219) and returns the process to Step S217. Accordingly, the user is notified of the fact that the inappropriate reagent is installed in the holder section and the installation of an appropriate reagent is prompted.

On the other hand, in Step S218, when the replaced reagent is appropriate (YES in Step S218), the CPU 51*a* reads out a notification message MS from the hard disk 51*d* and displays the notification message "The appropriate reagent container has been set. Please close the cover." on the image display section 52 (Step S220). In this case, when another notification message is displayed on the image display section with the emission of the alarm sound, the CPU 51*a* ends the display of the other notification message and stops the emission of the alarm sound.

Next, the CPU 51*a* determines whether the cover 63 is closed by an output signal of the cover opening/closing sensor 63*a* (Step S221). When the closing of the cover 63 is not detected (NO in Step S221), the CPU 51*a* repeats the process of Step S221 until the closing of the cover 63 is detected.

On the other hand, when the closing of the cover 63 is detected in Step S221 (YES in Step S221), the CPU 51*a* ends the display of the notification message prompting the closing of the cover, which is displayed in Step S220 (Step S222), and registers the reagent information read out from the RFID tag 360 or 260 in the reagent management table RMT (Step S223). In this process, the reagent information corresponding to the installation position which has been stored in the reagent management table RMT, that is, the reagent information related to the reagent before the replacement is deleted and the reagent information read out from the RFID tag 360 or 260 is stored in association with the installation position indicating the holder section.

Next, the CPU 51*a* stops the driven RFID reader and ends the readout of the reagent information from the RFID tag 260 of the reagent container 200 or the RFID tag 360 of the reagent container 300, either of which is installed in the above holder section provided with the RFID reader (Step S224).

In addition, the CPU 51*a* executes a reagent replacement sequence (Step S225). The reagent replacement sequence is a control process of the first measuring unit 3 or the second measuring unit 2 to suction a predetermined amount of reagent from a replaced reagent container and discard the reagent collected as a result in the reaction chamber 22*a* in order to eliminate bubbles which are generated in the flow passage from the piercer 64 to the reaction chamber 22*a* due to the reagent replacement in the first measuring unit 3 or the second measuring unit 2.

When the reagent replacement sequence ends, the CPU 51*a* reads out a notification message MS from the hard disk 51*d* and displays the notification message "The reagent replacement has been completed." on the image display section 52 (Step S226). After elapse of a predetermined time from the display of the notification message in Step S226, the CPU 51*a* ends the display of the notification message (Step S227) and ends the reagent replacement control process.

Second Embodiment

[Configuration of Sample Analyzer]

Hereinafter, the configuration of a sample analyzer according to this embodiment will be described.

Figure 15:
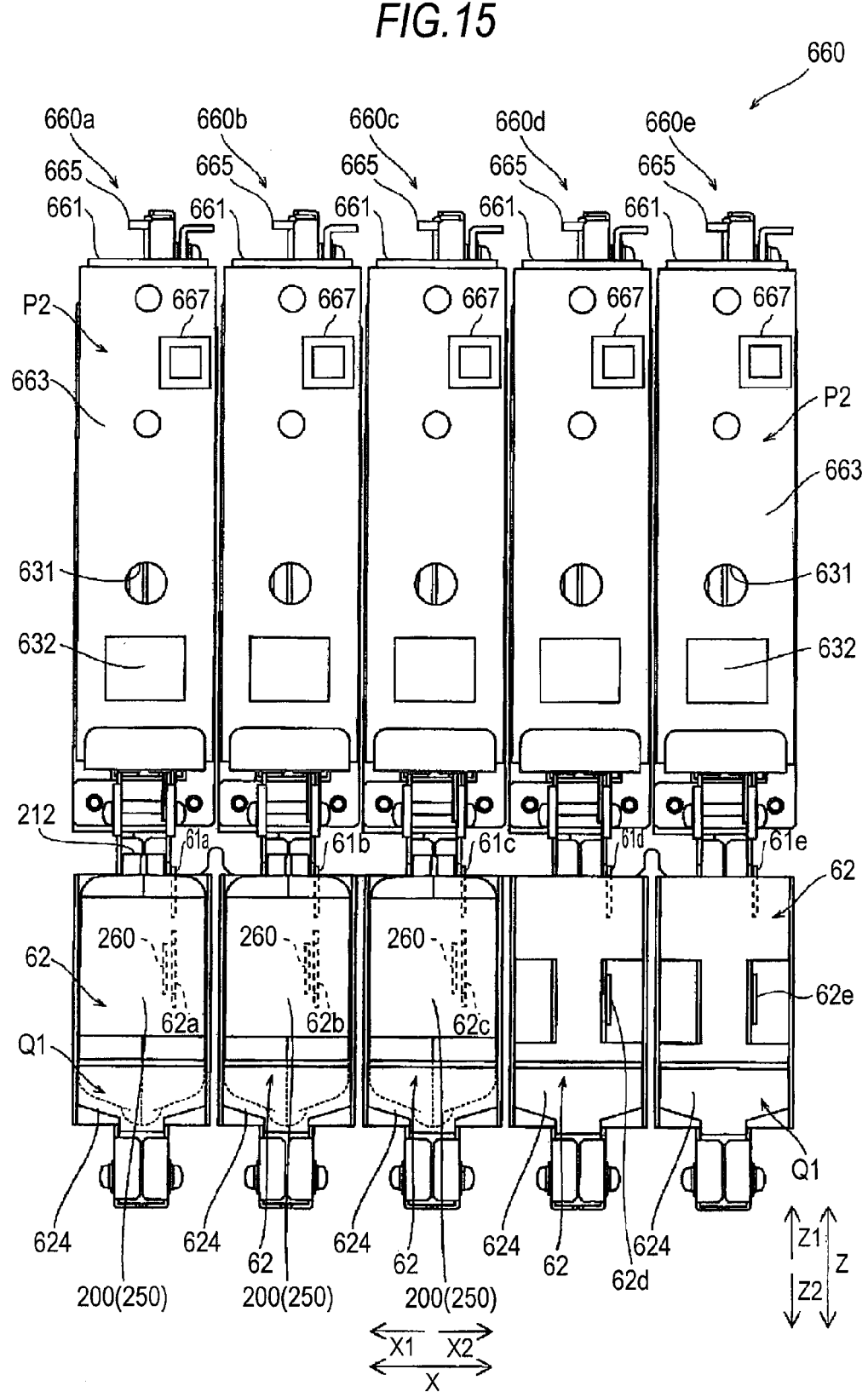
FIG. 15 is a front view showing the configuration of a reagent container holder of a measuring unit according to a second embodiment.

FIG. 15 is a front view showing the configuration of a reagent container holder of a second measuring unit according to this embodiment. As shown in FIG. 15, a reagent container holder 660 has five holder sections 660*a*, 660*b*, 660*c*, 660*d*, and 660*e* and is configured to hold a total of five (five kinds) reagent containers 200 (or 300). Each of the holder sections 660*a* to 660*e* has a chassis 661, a cover 663 for opening and closing a reagent container installation section 62, and a piercer lifting mechanism 665. A press button switch 667 is attached to the front surface of each cover 663.

Figure 16:
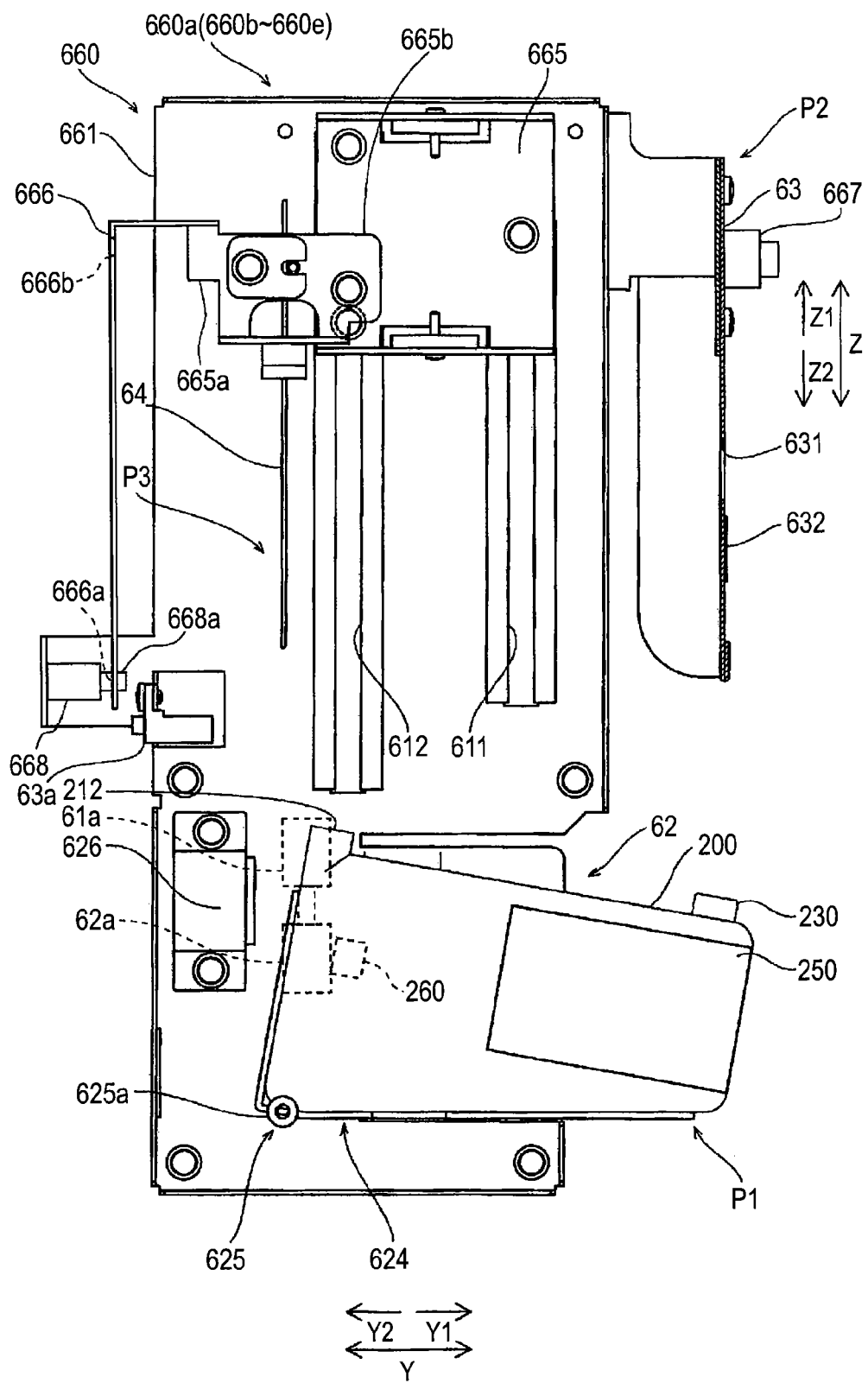
FIG. 16 is a vertical cross-sectional view showing the internal configuration of the reagent container holder according to the second embodiment.
Figure 17:
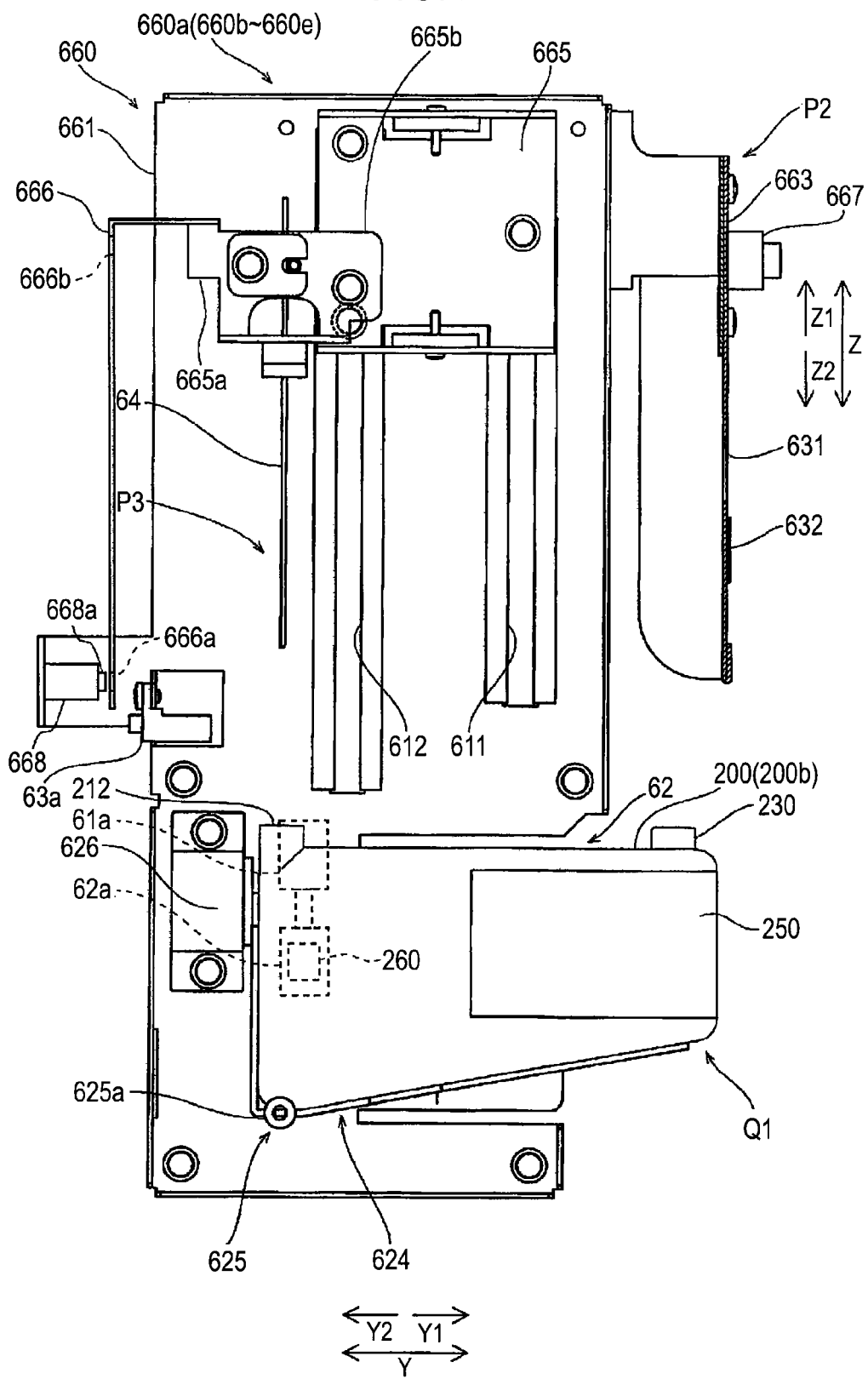
FIG. 17 is a vertical cross-sectional view showing the internal configuration of the reagent container holder according to the second embodiment.
Figure 18:
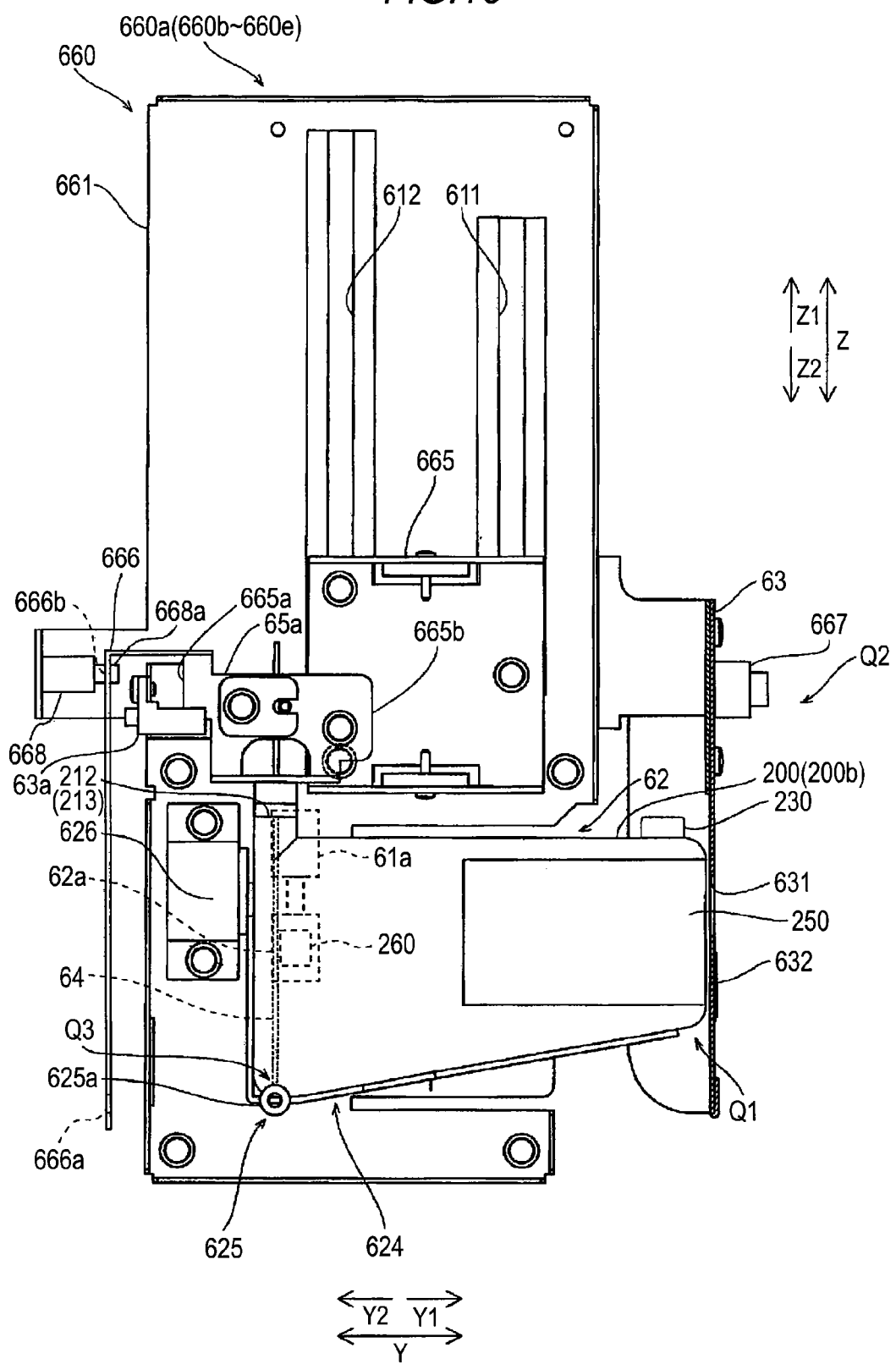
FIG. 18 is a vertical cross-sectional view showing the internal configuration of the reagent container holder according to the second embodiment.

FIGS. 16 to 18 are vertical cross-sectional views schematically showing the internal configuration of the reagent container holder according to this embodiment. FIG. 16 shows a state in which a reagent container is attached or removed in the reagent container holder. FIG. 17 shows a state in which a reagent container is set in the reagent container holder. FIG. 18 shows a state in which the cover of the reagent container holder is lowered. As shown in FIG. 16, the piercer lifting mechanism 665 is provided with a detecting piece 665*a* which is detected by a cover opening/closing sensor 63*a*. This detecting piece 665*a* is formed using a protruding portion of a support plate 665*b* supporting a piercer 64 and the support plate 665*b* continuously extends backward from the upper portion of the detecting piece 665*a*. Further, the support plate 665*b* is bent downward behind the detecting piece 665*a*, and the lower side from the bent portion is formed as a locking section 666 having a vertical plate shape. The locking section 666 is provided with a first locking hole 666*a* near the lower end thereof and a second locking hole 666*b* near the upper end thereof.

A solenoid support section 661*a* protrudes backward near the position at which the cover opening/closing sensor 63*a* of the chassis 661 is attached. Such a solenoid support section 661*a* is bent by 90 degrees at the tip end and supports a solenoid 668. The solenoid 668 has a rod-shaped plunger 668*a* and can move the plunger 668*a* by being driven. The plunger 668*a* is biased backward by a spring (not shown) built in the solenoid 668. When a current is not supplied to the solenoid 668, the plunger 668*a* is positioned at a locking release position accommodated in the main body of the solenoid 668. When a current is supplied to the solenoid 668, the plunger 668*a* moves forward due to an electromagnetic force. The moving end position at the front side of the plunger 668*a* is referred to as a locking position. That is, the solenoid 668 can displace the plunger 668*a* between the locking position and the locking release position.

When the cover 663 is opened and the piercer 64 is at a lifting position P3, the first locking hole 666*a* of the locking section 666 is opposed to the solenoid 668. At this time, when the solenoid 668 is driven and the plunger 668*a* comes to the locking position, the plunger 668a passes through the first locking hole 666a and the locking section 666 is fixed by the solenoid 668. Accordingly, the locking section is locked in a position where the cover 663 is opened (hereinafter, referred to as the "open position"). At this time, the cover 663 cannot be closed (see FIG. 16).

Meanwhile, when a current is not supplied to the solenoid, the plunger 668a is positioned at the locking release position and the plunger 668a is separated from the first locking hole 666a. Accordingly, the locking section 666 is not locked by the solenoid 668 and can move downward, and thus it can close the cover 663 (see FIG. 17).

When the cover 663 is closed and the piercer 64 is at a lowered position Q3, the second locking hole 666b of the locking section 666 is opposed to the solenoid 668. At this time, when the solenoid 668 is driven and the plunger 668a comes to the locking position, the plunger 668a passes through the second locking hole 666b and the locking section 666 is fixed by the solenoid 668. Accordingly, the locking section is locked in a position where the cover 663 is closed (hereinafter, referred to as the "closed position"). At this time, the cover 663 cannot be opened (see FIG. 18).

The solenoid 668 can be operated by operating the press button switch 667. When a predetermined cover 663 in the closed position is locked and a user opens this cover 663, the current supply to the solenoid 668 is stopped when the user presses the press button switch 667 provided in the cover 663. Accordingly, the plunger 668a is moved to the locking release position and the locking of the cover 663 is released. In this state, the user can open the cover 663.

Since the other configurations in the sample analyzer according to this embodiment are the same as those in the sample analyzer 1 according to the first embodiment, the same constituents will be denoted by the same symbols.

[Operation of Sample Analyzer]

Hereinafter, the operation of the sample analyzer according to this embodiment will be described.

<Sample Analysis Operation>

In the sample analyzer according to this embodiment, in a state in which the sample analyzer is powered off and is not started up, the solenoid 668 is not supplied with a current as described above and the locking of the respective covers 663 is released. Accordingly, in a state in which the sample analyzer is in the power-off state, a user can freely open and close the cover 663 and replace the reagent.

When power is applied to the sample analyzer and the sample analyzer is started up, the solenoid 668 is supplied with a current and the cover 663 is locked. In that state, the sample analyzer performs an initialization operation including a check of the operations of the mechanisms. In this initialization operation, the CPU 51a drives RFID readers 61a to 61e, reads reagent information from the RFID tags 360 and 260 of the reagent containers 300 and 200 which are installed in the respective reagent container holders 660 of a first measuring unit 3 and the second measuring unit 2, compares reagent codes included in the reagent information with reagent codes stored in a reagent code table, and determines whether the appropriate reagent is installed. In addition, in this process, it is also determined whether the remaining reagent of the reagent runs out, whether the expiration date of the reagent has expired and whether the expiry date after opening which is decided by an opening date of the reagent has expired, and on the basis of the determination, it is determined whether the installed reagent is appropriate. In this process, when the reagent is not appropriate, the CPU 51a executes the same process as a reagent replacement control process to be described later. However, since the sample measurement is not performed during the initialization operation, a measurement stop process of Step S302 is not executed.

When the initialization operation is completed, the sample analyzer enters a standby state to start the sample measurement. In this standby state, the supply of a current to each solenoid 668 is stopped and the locking of the covers 663 is released. Accordingly, in the standby state, a user can open and close the cover 663.

When an automatic sample analysis operation or a manual sample analysis operation is executed, a current is supplied again to each solenoid 668 and the covers 663 are locked. Accordingly, occurrence of abnormality in the operation due to the removal of a reagent container during the measurement operation of the first measuring unit 3 and the second measuring unit 2 is prevented.

Since the sample analysis operation in the sample analyzer according to this embodiment is the same as the sample analysis operation of the sample analyzer 1 according to the first embodiment, except that the cover 663 is locked during the measurement operation, the description thereof will be omitted.

<Reagent Replacement Operation>

Figure 19B:
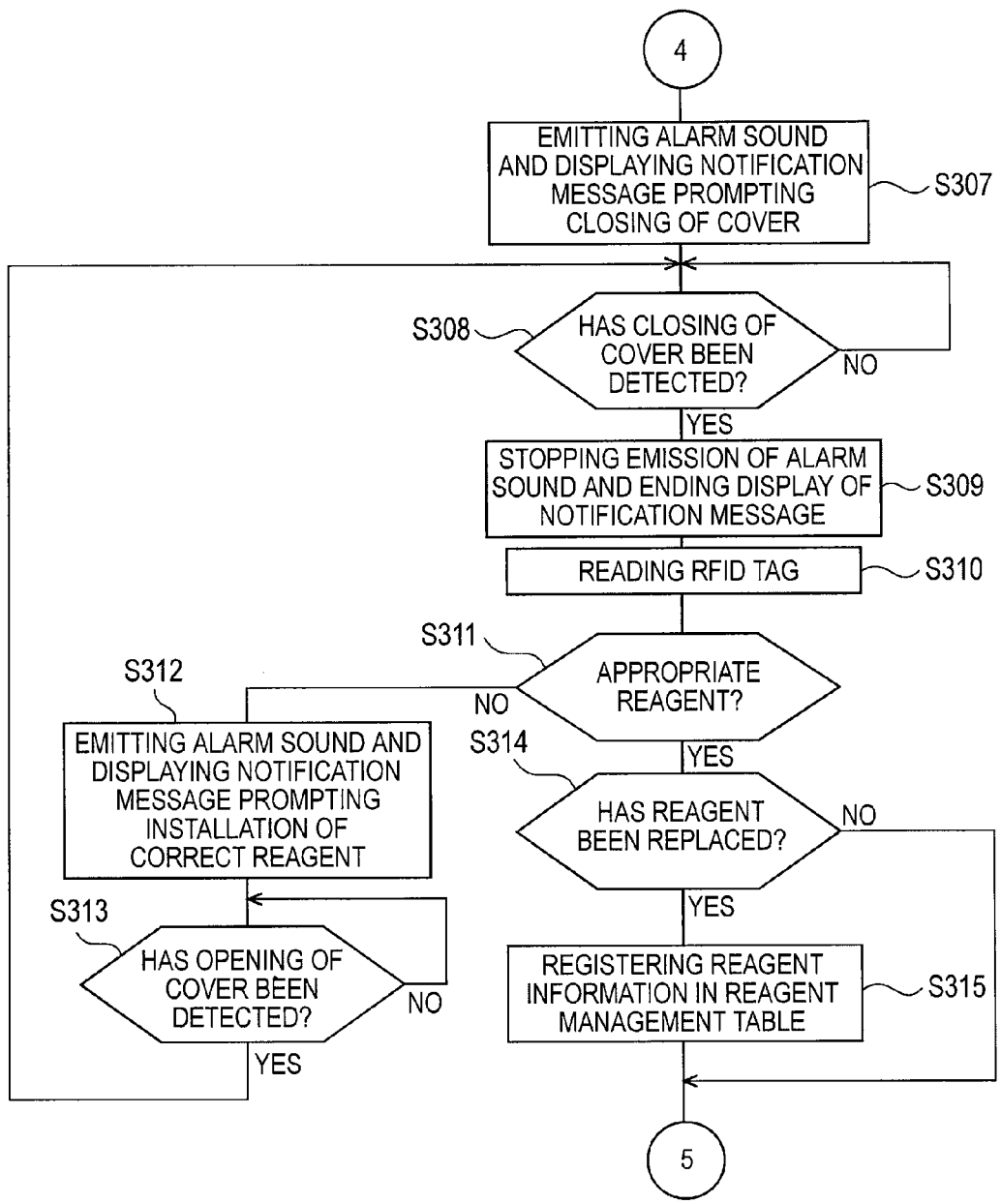
FIG. 19B is a flowchart showing the procedures of the reagent replacement control process of the information processing unit according to the second embodiment.
Figure 19C:
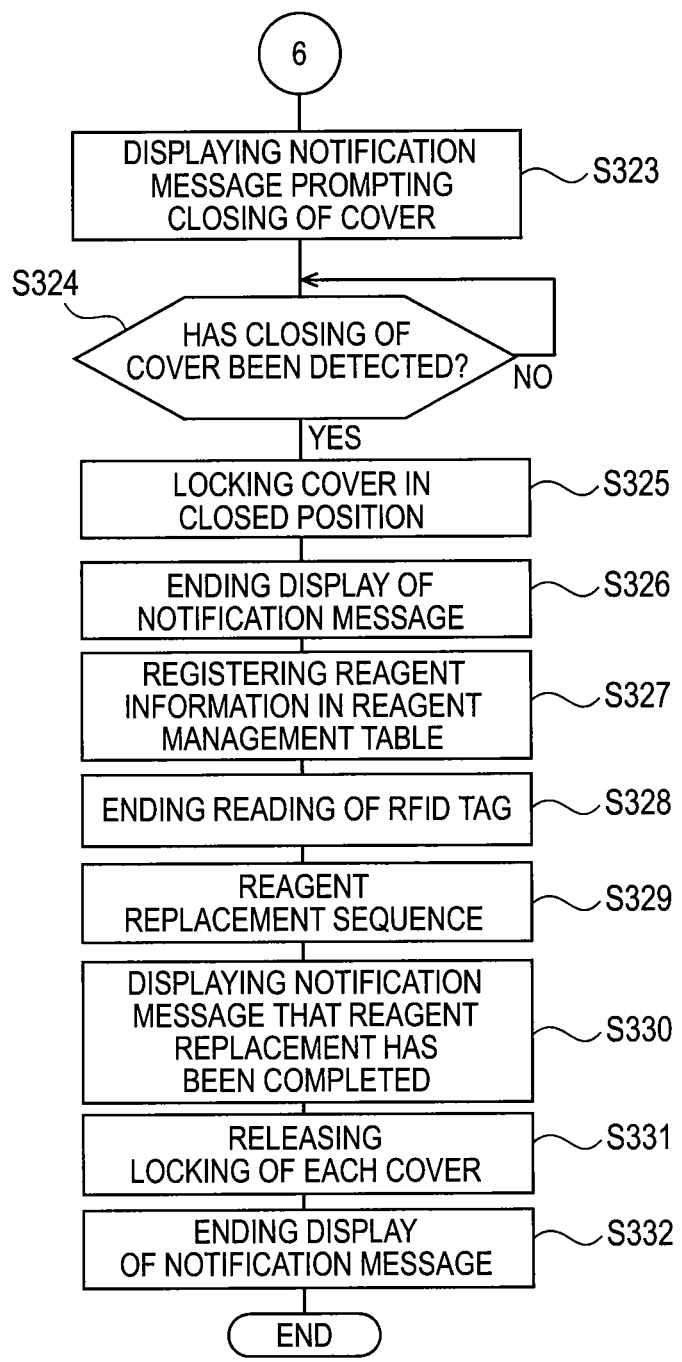
FIG. 19C is a flowchart showing the procedures of the reagent replacement control process of the information processing unit according to the second embodiment.

FIGS. 19A to 19C are flowcharts showing the procedures of a reagent replacement control process of an information processing unit 5 according to this embodiment. Since the processes of Steps 301 and 302 are the same as the processes of Steps S201 and S202 described in the first embodiment, the description thereof will be omitted.

When the measurement stop process ends, the CPU 51a stops the supply of a current to each solenoid 668 and releases the locking of each cover 663 (Step S303). Accordingly, the cover 663 can be opened and closed. Since the processes of Steps S304 to S316 are the same as the processes of Steps S203 to S215 described in the first embodiment, the description thereof will be omitted.

In Step S316, when the display of the notification message prompting the replacement of the reagent ends, the CPU 51a supplies a current to the solenoid 668 corresponding to the opened cover 663 and locks the cover 663 in the open position (Step S317). Accordingly, in the case in which the reagent is not replaced, and in the case in which the appropriate reagent is not installed, the closing of the cover 663 is prevented and the reagent replacement is appropriately and reliably performed. Since the processes of Steps S318 to S321 are the same as the processes of Steps S216 to S219 described in the first embodiment, the description thereof will be omitted.

In Step S320, when the replaced reagent is appropriate (YES in Step S320), the CPU 51a stops the supply of a current to the solenoid corresponding to the cover 663 which is in the open position and releases the locking of the cover 663 (Step S322). Accordingly, the cover 663 can be closed after the installation of the appropriate reagent. Since the processes of Steps S323 and S324 are the same as the processes of Steps S220 and S221 described in the first embodiment, the description thereof will be omitted.

In Step S324, when the closing of the cover 663 is detected (YES in Step S324), the CPU 51a restarts the supply of a current to the solenoid 668 corresponding to the cover 663 of which the closing has been detected, and locks the cover 663 in the closed position (Step S325). Accordingly, re-replacement by a wrong reagent is prevented. Since the processes of Steps S326 to S330 are the same as the processes of Steps S222 to S226 described in the first embodiment, the description thereof will be omitted.

After the display of the notification message that the reagent replacement has been completed on the image display section 52 in Step S330, the CPU 51a stops the supply of a current to the respective solenoids 668 and releases the locking of the respective covers 663 (Step S331). After elapse of a predetermined time from the display of the notification message in Step S330, the CPU 51a ends the display of the notification message (Step S332) and ends the reagent replacement control process.

Due to the above-described configuration, in the sample analyzer according to the first and second embodiments, when it is required to replace a reagent container, in the case in which the opening of the cover 63 (663) provided in the reagent container installation section 62 for installing a reagent container different from the reagent container which is required to be replaced is detected, a notification message "A cover not corresponding to the replacement target has been opened. Please close the cover" is output to notify that the cover 63 (663) provided in the reagent container installation section 62 different from the reagent container installation section 62 corresponding to the reagent container replacement target has been opened. Accordingly, by confirming this notification message, a user can easily recognize that the reagent container is to be installed in the wrong reagent container installation section 62. In addition, since the above-described notification message also includes the text information "please close the cover" prompting the closing of the cover 63 (663), the user can easily recognize that the work to be done next is closing of the opened cover 63 (663).

In addition, when a new reagent container is installed in the reagent container installation section 62, in the case in which the reagent code of the above reagent and the reagent code of the reagent to be installed in the above reagent container installation section 62 in the reagent code table RCT match and the installed reagent container is not a reagent container containing a reagent to be installed in the reagent container installation section 62, a notification message "Please set an appropriate reagent container." is output to prompt the installation of another reagent container. Accordingly, the user can easily recognize that the appropriate reagent container has not been installed and can easily recognize that work to be done next is installation of the appropriate reagent container.

Other Embodiments

In the above-described first and second embodiments, the configuration has been described in which the reagent replacement operation is executed when the sample analyzer determines that the replacement of the reagent is needed, but the invention is not limited thereto. A configuration may be provided in which the reagent replacement operation is executed when the sample analyzer receives a reagent replacement instruction from a user. In addition, for example, when a reagent container is not installed in the reagent container installation section 62 which is an installation target in which a user wants to install a reagent and an instruction for installing a reagent in the reagent container installation section 62 which is the installation target is received from the user, the reagent replacement operation may be executed. At this time, a notification message "A cover not corresponding to the installation target has been opened. Please close the cover." may be output to notify that the cover 63 (663) provided in a reagent container installation section 62 different from the reagent container installation section 62 which is the target in which the reagent container is to be installed has been opened.

In addition, in the above-described first and second embodiments, the configuration has been described in which it is determined whether the appropriate reagent has been installed in Steps S210, S218, S311, and S320, but the invention is not limited thereto. A configuration may be provided in which these steps are omitted and determination whether the appropriate reagent has been installed is not executed.

In addition, in the above-described first and second embodiments, the configuration has been described in which the cover 63 (663) and the piercer 64 are connected to each other by the piercer lifting mechanism 65 and the cover 63 (663) and the piercer 64 are integrally lifted and lowered due to the user's operation, but the invention is not limited thereto. A configuration may be provided in which a driving source such as a motor for lifting and lowering the piercer 64 is provided, and when the cover 63 (663) is moved in the vertical direction, the information processing unit 5 controls the driving source to lift and lower the piercer 64 in conjunction with the lifting and lowering of the cover 63 (663). A configuration may also be provided in which the piercer 64 is lifted and lowered independently from the cover 63 (663).

In addition, in the above-described first and second embodiments, the configuration has been described in which the notification is performed by emitting an alarm sound in addition to the notification message in Steps S206, S211, S219, S307, S312, and S321, but the invention is not limited thereto. A configuration may also be provided in which only a notification message is output without the emission of an alarm sound. A configuration may also be provided in which only an alarm sound is output without the output of a notification message.

In addition, in the above-described first and second embodiments, the configuration has been described in which each of the first and second measuring units takes a sample container 100 into the unit and a sample is suctioned from the sample container 100 in the unit, but the invention is not limited thereto. A configuration may be provided in which the first measuring unit directly suctions a sample from a sample container 100 on the sample transport unit. A configuration may also be provided in which the second measuring unit directly suctions a sample from a sample container 100 on the sample transport unit.

In addition, in the above-described first and second embodiments, the configuration has been described in which the opening of the cover 63 (663) is detected when the cover rises even slightly, and the closing of the cover 63 (663) is detected when the cover is completely closed, but the invention is not limited thereto. The opening of the cover 63 (663) may be detected when the cover 63 (663) is completely opened, and the closing of the cover 63 (663) may be detected when the cover 63 (663) lowers even slightly from the complete opening state. In addition, the opening of the cover 63 (663) may be detected when the cover 63 (663) rises up to a predetermined height, and the closing of the cover 63 (663) may be detected when the cover 63 (663) lowers up to the predetermined height.

In addition, in the above-described first and second embodiments, the configuration has been described in which the cover opening/closing sensor 63a detects the operation of installing a reagent container, but the invention is not limited thereto. For example, the operation of installing a reagent container can be detected by detecting the movement of the piercer 64 or by detecting the rotation of the support section 624. The operation of installing a reagent container may be detected by detecting that a reagent container 200 (300) is taken out of the holder sections 60a to 60e. Taking the reagent container 200 (300) out of the holder sections 60a to 60e can be detected by a change in the reading result of the RFID tag of the reagent container 200 (300).

In addition, in the above-described first and second embodiments, the configuration has been described in which the sample analyzer includes the two measuring units which are the first measuring unit and the second measuring unit, but the invention is not limited thereto. The sample analyzer may include three or more measuring units and may include a single measuring unit.

In addition, in the above-described first and second embodiments, the configuration has been described in which the information processing unit which is provided independently of the first measuring unit, the second measuring unit, and the sample transport unit controls the first measuring unit, the second measuring unit, and the sample transport unit, but the invention is not limited thereto. A configuration may be provided in which a control substrate equipped with a CPU, a memory, and the like is provided in each of the first measuring unit, the second measuring unit, and the sample transport unit, the respective control substrates are connected to the information processing unit so as to communicate therewith and the control substrates control the respective mechanism sections of the first measuring unit, the second measuring unit, and the sample transport unit, in accordance with a command transmitted from the information processing unit.

In addition, in the above-described first and second embodiments, the configuration has been described in which the sample analyzer includes the information processing unit which is provided independently of the first measuring unit and the second measuring unit, but the invention is not limited thereto. The sample analyzer may be an integrated sample analyzer equipped with the measuring units and the information processing unit in a single casing.

In addition, in the above-described embodiments, the example is shown in which the invention is applied to a multiple blood cell analyzer, but the invention is not limited thereto. The invention may be applied to a sample analyzer other than the multiple blood cell analyzer, such as a blood coagulation measurement device, an immunological analyzer, an in-urine physical component analyzer, a urine qualitative analyzer or a biochemical analyzer, which analyzes a sample by using a plurality of kinds of reagents. In this case, a reagent container which is installed in the reagent container installation section is not limited to a reagent container containing a staining liquid for blood cell analysis. In the case of a blood coagulation measurement device, a reagent container containing a reagent for blood coagulation measurement may be installed in the reagent container installation section. In the case of an in-urine physical component analyzer, a reagent container containing a reagent for in-urine physical component analysis may be installed in the reagent container installation section. In the case of a urine qualitative analyzer, a reagent container containing a reagent for urine qualitative analysis may be installed in the reagent container installation section. In the case of a biochemical analyzer, a reagent container containing a reagent for biochemical analysis may be installed in the reagent container installation section. In the case of an immunological analyzer, a reagent container containing a reagent for immunological analysis may be installed in the reagent container installation section. In addition, a configuration may also be provided in which a reagent container containing a reagent other than a staining liquid for blood cell analysis, for example, a hemolytic agent is installed in the reagent container installation section in the multiple blood cell analyzer. In addition, the invention can be preferably applied to a particle analyzer including a flow cytometer. Examples of the particle analyzer including a flow cytometer include a multi-item blood cell analyzer, an in-urine physical component analyzer, a blood cancer cell analyzer, and the like. In the above-described particle analyzer, particles of a detection target are stained using a plurality of kinds of staining reagents. Accordingly, the fluid system is easily contaminated with the staining reagents and the number of kinds of the staining reagents is not large as in the case of a biochemical analyzer. Therefore, the position for installing each staining reagent in the analyzer is determined for each kind of the staining reagent, and the staining reagent does not move from the installation position when the particle analyzer is used. In this manner, in the sample analyzer, since the staining reagent installation position is determined for each kind of the staining reagent, it is useful that a user can more precisely install a reagent container than in conventional cases in comparison with an analyzer other than the particle analyzer.

In addition, in the above-described embodiments, the configuration has been described in which the single computer $5a$ executes all the processes of the computer program $54a$, but the invention is not limited thereto. The same process as the above-described computer program $54a$ may be dispersed to a plurality of devices (computers) and executed.

INDUSTRIAL APPLICABILITY

The sample analyzer of the invention is useful as a sample analyzer which analyzes a sample by using a reagent.

What is claimed is:
1. A sample analyzer comprising:
a specimen preparation section that includes:
  a first reagent container containing a first reagent,
  a second reagent container containing a second reagent, and
  a sample container including a blood cell,
wherein the specimen preparation section prepares:
  a first measurement specimen from the first reagent contained in the first reagent container and the sample including a blood cell, and
  a second measurement specimen from the second reagent contained in the second reagent container and the sample,
wherein the first reagent container includes a first recording medium storing a first reagent information indicating the first reagent, and the second reagent container includes a second recording medium storing a second reagent information indicating the second reagent;
a detecting section that includes a flow cell into which the first and second measurement specimens are introduced, wherein the detecting section detects the blood cell from the first measurement specimen, the second measurement specimen, or both passing through the flow cell;
a first container set section that receives the first reagent container;
a first cover that moves to a first open position where the setting of the first reagent container in the first container set section is permitted and a first closed position where the setting of the first reagent container in the first container set section is not permitted;
a first detector that detects a movement of the first cover to the first open position;
a second container set section that receives the second reagent container;
a second cover that moves to a second open position where the setting of the second reagent container in the second container set section is permitted and a second closed position where the setting of the second reagent container in the second container set section is not permitted;

a second detector that detects a movement of the second cover to the second open position;
a first information reader that reads information from a recording medium of a reagent container set in the first container set section;
a second information reader that reads information from a recording medium of a reagent container set in the second container set section;
an output section; and
a controller programmed to:
control the output section to output a predetermined notification, if the second detector detects the movement of the second cover to the second open position when it is required to set the first reagent container in the first container set section; and
control the first information reader to start reading the information when the first detector detects a movement of the first cover to the first open position.

2. The sample analyzer according to claim 1, wherein the predetermined notification includes a message notifying that the second cover has been opened by a user.

3. The sample analyzer according to claim 1, wherein the controller is further programmed to determine whether the first reagent container is appropriate based on the information that has been read from the recording medium of the reagent container set in the first container set section by the first information reader.

4. The sample analyzer according to claim 3, wherein the controller is further programmed to control the output section to output a message prompting a user to set another reagent container in the first container set section if the reagent container set in the first container set section is determined to be inappropriate.

5. The sample analyzer according to claim 3, wherein the controller is further programmed to control the output section to output a message prompting a user to close the first cover if the reagent container set in the first container set section is determined to be appropriate.

6. The sample analyzer according to claim 1, wherein if the controller determines that the reagent container set in the first container set section is appropriate and the first detector detects a movement of the first cover to the first closed position, the controller is further programmed to start an operation to make sample analysis using the first reagent ready.

7. The sample analyzer according to claim 1, further comprising:
a first suction tube that suctions the first reagent from the first reagent container set in the first container set section;
a second suction tube that suctions the second reagent from the second reagent container set in the second container set section;
a first piercer lifting mechanism that moves the first suction tube in conjunction with a movement of the first cover so that the first suction tube retreats from the first reagent container when the first cover is moved to the first open position and the first suction tube advances into the first reagent container when the first cover is moved to the first closed position; and
a second piercer lifting mechanism that moves the second suction tube in conjunction with a movement of the second cover so that the second suction tube retreats from the second reagent container when the second cover is moved to the second open position and the second suction tube advances into the second reagent container when the second cover is moved to the second closed position.

8. The sample analyzer according to claim 1, wherein the controller is further programmed to determine whether the first reagent container or the second reagent container is required to be replaced based on information regarding a remaining reagent amount, information regarding an expiration date, or both.

9. The sample analyzer according to claim 1, wherein the first and second container set sections have the same shape, and the first and second covers have the same shape.

10. The sample analyzer according to claim 1, wherein the first reagent container contains a staining liquid for staining the blood cell.

11. The sample analyzer according to claim 1, wherein the controller is further programmed to determine whether it is required to replace the first reagent container in the first container set section based on the information read from the recording medium of the first reagent container by the first information reader, and programmed to determine whether it is required to replace the second reagent container in the second container set section based on the information read from the recording medium of the second reagent container by the second information reader.

12. The sample analyzer according to claim 1, wherein the controller is programmed to control the output section to output a predetermined notification, if a replaced reagent is not appropriate.

13. The sample analyzer according to claim 1, wherein the controller is programmed to control the first information reader to stop reading the information when the first detector detects a movement of the first cover to the first closed position.

* * * * *